(12) United States Patent
Smith et al.

(10) Patent No.: US 10,206,396 B2
(45) Date of Patent: *Feb. 19, 2019

(54) AGRICULTURAL COMPOSITIONS COMPRISING CHITIN OLIGOMERS

(71) Applicant: NOVOZYMES BIOAG A/S, Bagsvaerd (DK)

(72) Inventors: R. Stewart Smith, Pewaukee, WI (US); Ahsan Habib, Roanoke, VA (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,507

(22) Filed: Jul. 11, 2016

(65) Prior Publication Data

US 2016/0316748 A1    Nov. 3, 2016

Related U.S. Application Data

(63) Continuation of application No. 14/709,769, filed on May 12, 2015, now Pat. No. 9,414,592, which is a continuation of application No. 13/625,393, filed on Sep. 24, 2012, now Pat. No. 9,055,746.

(60) Provisional application No. 61/538,326, filed on Sep. 23, 2011.

(51) Int. Cl.
| | |
|---|---|
| *A01N 43/16* | (2006.01) |
| *A01N 63/00* | (2006.01) |
| *C05F 11/00* | (2006.01) |
| *A01N 63/02* | (2006.01) |
| *A01N 63/04* | (2006.01) |

(52) U.S. Cl.
CPC .............. *A01N 43/16* (2013.01); *A01N 63/00* (2013.01); *A01N 63/02* (2013.01); *A01N 63/04* (2013.01); *C05F 11/00* (2013.01)

(58) Field of Classification Search
CPC .................................. C05F 11/00; C05F 11/08
See application file for complete search history.

(56) References Cited

U.S. PATENT DOCUMENTS

| | | |
|---|---|---|
| 4,536,207 A | 8/1985 | McCandliss |
| 4,804,750 A | 2/1989 | Nishimura |
| 4,812,159 A | 3/1989 | Freepons |
| 4,886,541 A | 12/1989 | Hadwiger |
| 4,940,840 A | 7/1990 | Suslow |
| 4,964,894 A | 10/1990 | Freepons |
| 4,978,381 A | 12/1990 | Hadwiger |
| 5,026,417 A | 6/1991 | Kucey |
| 5,057,141 A | 10/1991 | Rodriguez-Kabana |
| 5,104,437 A | 4/1992 | Hadwiger |
| 5,141,745 A | 8/1992 | Rolfe |
| 5,175,149 A | 12/1992 | Stacey |
| 5,321,011 A | 6/1994 | Stacey |
| 5,374,627 A | 12/1994 | Ito |
| 5,454,464 A | 10/1995 | Yamamoto |
| 5,536,155 A | 7/1996 | Futaki |
| 5,549,718 A | 8/1996 | Lerouge |
| 5,554,445 A | 9/1996 | Struszczyk |
| 5,586,411 A | 12/1996 | Gleddie |
| 5,628,810 A | 5/1997 | Dugast |
| 5,646,018 A | 7/1997 | Broughton |
| 5,696,098 A | 12/1997 | Muraki |
| 5,702,752 A | 12/1997 | Gugger |
| 5,705,634 A | 1/1998 | Bredehorst |
| 5,720,793 A | 2/1998 | Kato |
| 5,726,123 A | 3/1998 | Heinsohn |
| 5,733,851 A | 3/1998 | Villanueva |
| 5,830,459 A | 11/1998 | Cuero |
| 5,922,316 A | 7/1999 | Smith |
| 5,965,545 A | 10/1999 | Ben-Shalom |
| 5,990,291 A | 11/1999 | Waggle |
| 6,060,429 A | 5/2000 | Ben-Shalom |
| 6,146,668 A | 11/2000 | Kelly |
| 6,167,652 B1 | 1/2001 | Heinsohn |
| 6,193,988 B1 | 2/2001 | Stoner |
| 6,197,942 B1 | 3/2001 | Muraki |
| 6,200,929 B1 | 3/2001 | Horibe |
| 6,242,381 B1 | 6/2001 | van der Krieken |
| 6,258,749 B1 | 7/2001 | Nonomura |
| 6,306,835 B1 | 10/2001 | Daly |
| 6,352,727 B1 | 3/2002 | Takahashi |
| 6,407,040 B1 | 6/2002 | Nichols |

(Continued)

FOREIGN PATENT DOCUMENTS

| | | |
|---|---|---|
| CA | 2202024 A1 | 10/1998 |
| CN | 101092315 A | 12/2007 |

(Continued)

OTHER PUBLICATIONS

Halford et al, 2010, Chem Eng New 88 (15), 37-38.
Maj et al, 2009, J Chem Ecol 35, 479-487—(Spec).
Noreen et al. 2003, Func Plant Biol 30, 1219-1232.
Hamid et al. 2013, J. Pharm. Bioallied Sci Jan.-Mar. 5(1), 21-29.
Nishizawa et al. 1999, Plant Molecular Biology 39, 907-914.
Ramonell et al. 2005, Plant Physiology 138, 1027-1036.
Wan et al. 2008, The Plant Cell 20, 471-481.
Zhang et al. 2002, MPMI 15(9), 963-970.

(Continued)

*Primary Examiner* — Sreenivasan Padmanabhan
*Assistant Examiner* — Genevieve S Alley
(74) *Attorney, Agent, or Firm* — Adam Rucker

(57) ABSTRACT

Disclosed are methods of enhancing plant growth, comprising treating plant seed or the plant that germinates from the seed with an effective amount of at least one chitooligosaccharide, wherein upon harvesting the plant exhibits at least one of increased plant yield measured in terms of bushels/acre, increased root number, increased root length, increased root mass, increased root volume and increased leaf area, compared to untreated plants or plants harvested from untreated seed.

20 Claims, 31 Drawing Sheets

(56) References Cited

U.S. PATENT DOCUMENTS

| | | |
|---|---|---|
| 6,413,910 B1 | 7/2002 | Vasiljevich |
| 6,524,998 B1 | 2/2003 | Kloepper |
| 6,589,352 B1 | 7/2003 | Yudovsky |
| 6,589,942 B1 | 7/2003 | Ben-Shalom |
| 6,630,459 B2 | 10/2003 | Vournakis |
| 6,649,566 B2 | 11/2003 | Doostdar |
| 6,849,576 B2 | 2/2005 | Suzuki |
| 6,878,819 B1 | 4/2005 | Natunen |
| 6,933,380 B2 | 8/2005 | Huang |
| 6,979,664 B1 | 12/2005 | Smith |
| 7,098,324 B2 | 8/2006 | Haigler |
| 7,205,450 B2 | 4/2007 | Cook |
| 7,250,068 B1 | 7/2007 | Smith |
| 7,262,151 B2 | 8/2007 | Smith |
| 7,485,718 B2 | 2/2009 | Sabesan |
| 7,521,212 B1 | 4/2009 | Samain |
| 7,576,213 B2 | 8/2009 | Flematti |
| 7,619,076 B2 | 11/2009 | Beau |
| 7,637,980 B2 | 12/2009 | Smith |
| 7,670,820 B2 | 3/2010 | Shaw |
| 8,008,544 B2 | 8/2011 | Block |
| 8,357,631 B2 | 1/2013 | Smith |
| 8,946,119 B2 | 2/2015 | Smith |
| 8,992,653 B2 | 3/2015 | Smith |
| 9,055,746 B2 | 6/2015 | Smith |
| 2002/0000540 A1 | 1/2002 | Smither-Kopperl |
| 2002/0076402 A1* | 6/2002 | Khouri ............... A01N 63/02 424/94.61 |
| 2005/0187107 A1 | 8/2005 | Smith |
| 2006/0277632 A1 | 12/2006 | Carr |
| 2007/0027032 A1 | 2/2007 | Chen |
| 2007/0105815 A1 | 5/2007 | Vournakis |
| 2007/0238872 A1 | 10/2007 | Sabesan |
| 2008/0057093 A1 | 3/2008 | Wan |
| 2008/0072494 A1 | 3/2008 | Stoner |
| 2008/0172763 A1 | 7/2008 | Jensen |
| 2008/0248953 A1 | 10/2008 | Smith |
| 2008/0269055 A1 | 10/2008 | Bastiaans |
| 2009/0305895 A1 | 12/2009 | McIver |
| 2010/0031388 A1 | 2/2010 | Tirichine |
| 2010/0048404 A1 | 2/2010 | Hungenberg |
| 2010/0087369 A1 | 4/2010 | Cutsem |
| 2010/0093537 A1 | 4/2010 | Smith |
| 2010/0099560 A1 | 4/2010 | Hnatowich |
| 2010/0113278 A1 | 5/2010 | Suty-Heinze |
| 2011/0301032 A1 | 12/2011 | Denarie |
| 2012/0077674 A1 | 3/2012 | Cargeeg |
| 2012/0322659 A1 | 12/2012 | Smith |
| 2013/0061645 A1 | 3/2013 | Smith |
| 2013/0109567 A1 | 5/2013 | Smith |
| 2014/0342904 A1* | 11/2014 | Frodyma ............... A01N 63/00 504/100 |

FOREIGN PATENT DOCUMENTS

| | | |
|---|---|---|
| CN | 101248797 A | 8/2008 |
| CN | 101543230 A | 9/2009 |
| CN | 101601410 A | 12/2009 |
| FR | 2941591 A1 | 3/2009 |
| JP | 8003010 A2 | 1/1996 |
| WO | 89/007395 A1 | 8/1989 |
| WO | 92/17591 A1 | 10/1992 |
| WO | 1994/11006 A1 | 5/1994 |
| WO | 1995/015343 A1 | 6/1995 |
| WO | 98/34464 A2 | 8/1998 |
| WO | 00/004778 A1 | 2/2000 |
| WO | 01/26465 A1 | 4/2001 |
| WO | WO 2003/026677 * | 4/2003 |
| WO | 2003/077654 A1 | 9/2003 |
| WO | 2004/093542 A1 | 11/2004 |
| WO | 2005/62899 A1 | 7/2005 |
| WO | 2005/63784 A1 | 7/2005 |
| WO | 2005/087005 A1 | 9/2005 |
| WO | 2006/102717 A1 | 10/2006 |
| WO | 2007/006318 A2 | 1/2007 |
| WO | 2008/85958 A1 | 7/2008 |
| WO | 2009/049747 A2 | 4/2009 |
| WO | 2010/037167 A1 | 4/2010 |
| WO | 2010/49751 A1 | 5/2010 |
| WO | 2010/125065 A2 | 11/2010 |

OTHER PUBLICATIONS van der Holst et al. 2001. Current Opinions in Structural Biology 11, 608-616.
Robina et al. 2002 Tetrahedron 58, 521-530.
Samain et al. 1999, Journal of Biotechnology 72, 33-47.
Samain et al 1997, Carbohydrate Research 302, 35-42.
Cottaz et al 2005, Metabolic Engineering 7, 311-317.
Dumon et al 2006, ChemBioChem 7, 359-365.
Denaire et al 1996, Annu. Rev. Biochem. 65, 503-535.
Khan et al 2002, Photosynthetica 40(4), 621-624.
Jung et al 2007, Carbohydrate Polymers 67, 256-259.
Yoshikawa et al 1993, Plant Cell Physiol. 34(8), 1163-1173.
Hamel et al 2010, Planta 232, 787-806.
Okada et al 2002, Plant Cell Physiol 43(5), 505-512.
Muller et al 2000, Plant Physiology 124, 733-739.
Prome et al 1998, Pure & Appl. Chem. 70(1), 55-60.
Newsmart webpage re COS, www.glucosamine-chitosan.com (2005).
Darvill et al 1992, Glycobiology 2(3), 181-198.
Cote et al 1994, Plant Molecular Biology 26, 1379-1411.
Kasprezewska 2003, Cellular & Molecular Biology Letters 8, 809-824.
Cote et al 1995, Physiologiz Plantarium 93, 401-410.
Raiford 2010, "Smoke Signals", Chemical & Engineering News 88(15), 1-3.
D'Haeze et al 2002, Glycobiology 12(6), 79R-105R.
Demont-Caulet et al 1999, Plant Physiology 120, 83-92.
Maillet et al 2011, Nature 469, 58-64.
Macchiavelli et al 2004, Journal of Experimental Botany 55(408), 2635-2640.
Spaink 2000, Annu. Rev. Micriobiol 54, 257-288.
Pochanavanich et al 2002, Letters in Applied Microbiology 35, 17-21.
Shaw et al 2006, Environmental Microbiology 8(11), 1867-1880.
Ralston et al 2005, Plant Physiology 137, 1375-1388.
Wakelin et al 2004, Biol Fertil Soils 40, 36-43.
Diaz et al 2000, Molecular Plant-Microbe Interactions 13(3), 268-276.
Hungria et al 1997, Soil Biol. Biochem. 29(5/6), 819-830.
Friesen et al 2005, Appl Microbiol Biotechnol 68, 397-404.
Ferguson et al 2003, J Plant Growth Regul 22, 47-72.
Collinge et al 1993, The Plant Journal 3(1), 31-40.
Leibovitch et al 2001, J Agronomy & Crop Science 187, 281-292.
Pederson presentation Iowa State University "Soybean Growth and Development" (2009).
Prithiviraj et al 2003, Planta 216, 437-445.
Staehelin et al 1994, Proc. Natl. Acad. Sci. USA 91, 2196-2200.
Cytryn et al, 2007, J Bacteriology, 189(19), 6751-6762.
Deaker et al., 2007, Soil Biology & Biochemistry 39 573-580.
LePrince et al, 2010, Plant Science 179 554-564.
Mabood et al, 2006, Field Crops Research, 95 412-419.
Mary et al, 1994, Soil Biol Biochem 26(9), 1125-1132.
Radwan et al, 2007, Intl J Phytoremediation 9, 475-486.
Streeter, 2003, J Appl Microbiol 95, 484-491.
Sugawara et al, 2010, Appl Environ Microbiol 76(4), 1071-1081.
Supanjani et al, 2006 Plant Physiology and Biochemistry, 44 866-872.
Zahran., 2001, Journal of Biotechnology, 91 143-153.
Yong et al, 2011, Fine Chem 28(5), 479-483, Abstract only.
Jian-ping et al, 2011, J Anhui Agric Sci 39(1), 88-89, Abstract only.
Yuan Jian-Ping et al, 2011, J Anhui Agric Sci, vol. 39, No. 1, pp. 88-89.
Ma Peng Peng, 2001, Plant Physiology and Agriculture, vol. 37, No. 5 pp. 475-478.
Kim et al, 2013, Carbohydr Res, vol. 372, pp. 23-29.
Aam et al, 2010, Marine Drugs 8, 1482-1517.

(56) References Cited

OTHER PUBLICATIONS

Cho et al, 2008, J Food Sci 73(1), S70-S77.
Flematti et al, 2010, J Agric Food Chem 58, 8612-8617.
Kananont et al, 2010, Scientia Horticulturae 124, 239-247.
Limpanavech et al, 2008, Scientia Horticulturae 116, 65-72.
Mourya et al, 2011, Polymer Science Ser A 53(7), 583-612.
O'Callaghan et al, 2012, Agronomy New Zealand 42, 149-154.
Szymanska et al, 2015, Mar Drugs 13, 1819-1846.
Xia et al, 2011, Food Hydrocol 25, 170-179.

* cited by examiner

AGRICULTURAL COMPOSITIONS COMPRISING CHITIN OLIGOMERS

CROSS-REFERENCE TO RELATED APPLICATIONS

This application is a continuation of U.S. application Ser. No. 14/709,769 filed May 12, 2015, now allowed, which is a continuation of U.S. application Ser. No. 13/625,393 filed on Sep. 24, 2012, now U.S. Pat. No. 9,055,746, which claims priority or the benefit under 35 U.S.C. 119 of U.S. provisional application No. 61/538,326 filed Sep. 23, 2011, the contents of which are fully incorporated herein by reference.

BACKGROUND OF THE INVENTION

The symbiosis between the gram-negative soil bacteria, Rhizobiaceae and Bradyrhizobiaceae, and legumes such as soybean, is well documented. The biochemical basis for these relationships includes an exchange of molecular signaling, wherein the plant-to-bacteria signal compounds include flavones, isoflavones and flavanones, and the bacteria-to-plant signal compounds, which include the end products of the expression of the bradyrhizobial and rhizobial nod genes, known as lipo-chitooligosaccharides (LCOs). The symbiosis between these bacteria and the legumes enables the legume to fix atmospheric nitrogen for plant growth, thus obviating a need for nitrogen fertilizers. Since nitrogen fertilizers can significantly increase the cost of crops and are associated with a number of polluting effects, the agricultural industry continues its efforts to exploit this biological relationship and develop new agents and methods for improving plant yield without increasing the use of nitrogen-based fertilizers.

U.S. Pat. No. 6,979,664 teaches a method for enhancing seed germination or seedling emergence of a plant crop, comprising the steps of providing a composition that comprises an effective amount of at least one lipo-chitooligosaccharide and an agriculturally suitable carrier and applying the composition in the immediate vicinity of a seed or seedling in an effective amount for enhancing seed germination of seedling emergence in comparison to an untreated seed or seedling.

Further development on this concept is taught in WO 2005/062899, directed to combinations of at least one plant inducer, namely an LCO, in combination with a fungicide, insecticide, or combination thereof, to enhance a plant characteristic such as plant stand, growth, vigor and/or yield. The compositions and methods are taught to be applicable to both legumes and non-legumes, and may be used to treat a seed (just prior to planting), seedling, root or plant.

Similarly, WO 2008/085958 teaches compositions for enhancing plant growth and crop yield in both legumes and non-legumes, and which contain LCOs in combination with another active agent such as a chitin or chitosan, a flavonoid compound, or an herbicide, and which can be applied to seeds and/or plants concomitantly or sequentially. As in the case of the '899 Publication, the '958 Publication teaches treatment of seeds just prior to planting.

More recently, Halford, "Smoke Signals," in Chem. Eng. News (Apr. 12, 2010), at pages 37-38, reports that karrikins or butenolides which are contained in smoke act as growth stimulants and spur seed germination after a forest fire, and can invigorate seeds such as corn, tomatoes, lettuce and onions that had been stored. These molecules are the subject of U.S. Pat. No. 7,576,213.

There is, however, still a need for systems for improving or enhancing plant growth.

BRIEF SUMMARY OF THE INVENTION

A first aspect of the present invention is directed to a method of enhancing plant growth, comprising a) treating (e.g., applying to) plant seed or a plant that germinates from the seed, with an effective amount of at least one chitooligosaccharide (CO), wherein upon harvesting the plant exhibits at least one of increased plant yield measured in terms of bushels/acre, increased root number, increased root length, increased root mass, increased root volume and increased leaf area, compared to untreated plants or plants harvested from untreated seed.

In some embodiments, at least two CO's are used. In some embodiments, treatment of the seed includes direct application of the at least one CO onto the seed, which may then be planted or stored for a period of time prior to planting. Treatment of the seed may also include indirect treatment such as by introducing the at least one CO into the soil (known in the art as in-furrow application). In yet other embodiments, the at least one CO may be applied to the plant that germinates from the seed, e.g., via foliar spray. The methods may further include use of other agronomically beneficial agents, such as micronutrients, fatty acids and derivatives thereof, plant signal molecules (other than CO's), such as lipo-chitooligosaccharides, chitinous compounds (other than COs), flavonoids, jasmonic acid, linoleic acid and linolenic acid and their derivatives, and karrikins), herbicides, fungicides and insecticides, phosphate-solubilizing microorganisms, diazotrophs (Rhizobial inoculants), and/or mycorrhizal fungi, The methods of the present invention are applicable to legumes and non-legumes alike. In some embodiments, the leguminous seed is soybean seed. In some other embodiments, the seed that is treated is non-leguminous seed such as a field crop seed, e.g., a cereal such as corn, or a vegetable crop seed such as potato.

As demonstrated by the working examples, which summarize experiments conducted in both the greenhouse and in the field, the results achieved by the methods of the present invention show that application of at least one CO to seed or a plant that germinates from a seed, results in enhanced plant growth. These results are believed to be unexpected, particularly from the standpoint that COs were known to be involved in system acquired resistance (SAR) but not necessarily involved in the direct enhancement of plant growth. The results described herein show that in some cases, the inventive methods achieved a substantially equal effect or in some other cases, outperformed the enhancement of plant growth achieved by an LCO. The results obtained from the greenhouse experiments are particularly significant in this regard, in that they were conducted in substantially disease-free conditions.

DETAILED DESCRIPTION

Chitooligosaccharides

COs are known in the art as β-1-4 linked N-acetyl glucosamine structures identified as chitin oligomers, also as N-acetylchitooligosaccharides. CO's have unique and different side chain decorations which make them different from chitin molecules [$(C_8H_{13}NO_5)_n$, CAS No. 1398-61-4], and chitosan molecules [$(C_5H_{11}NO_4)_n$, CAS No. 9012-76-4]. See, e.g., Hamel, et al., Planta 232:787-806 (2010) (e.g., FIG. 1 which shows structures of chitin, chitosan, Nod factors (LCO's), and the corresponding CO's (which would lack the 18C, 16C, or 20C acyl group)). The CO's of the present invention are also relatively water-soluble compared to chitin and chitosan, and in some embodiments, as described hereinbelow, are pentameric. Representative literature describing the structure and production of COs that may be suitable for use in the present invention is as follows: Muller, et al., Plant Physiol. 124:733-9 (2000) (e.g., FIG. 1 therein); Van der Holst, et al., Current Opinion in Structural Biology, 11:608-616 (2001) (e.g., FIG. 1 therein); Robina, et al., Tetrahedron 58:521-530 (2002); D'Haeze, et al., Glycobiol. 12(6):79R-105R (2002); Rouge, et al. Chapter 27, "The Molecular Immunology of Complex Carbohydrates" in Advances in Experimental Medicine and Biology, Springer Science; Wan, et al., Plant Cell 21:1053-69 (2009); PCT/F100/00803 (Sep. 21, 2000); and Demont-Caulet, et al., Plant Physiol. 120(1):83-92 (1999).

CO's differ from LCO's in terms of structure mainly in that they lack the pendant fatty acid chain. Rhizobia-derived CO's, and non-naturally occurring synthetic derivatives thereof, that may be useful in the practice of the present invention may be represented by the following formula:

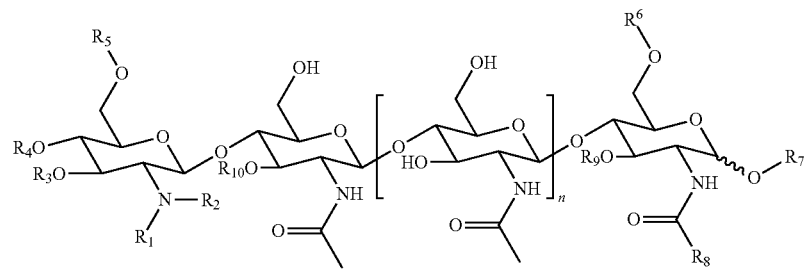

wherein $R_1$ and $R_2$ each independently represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc, and 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3. The structures of corresponding Rhizobial LCO's are described in D'Haeze, et al., supra.

Figure 1A:
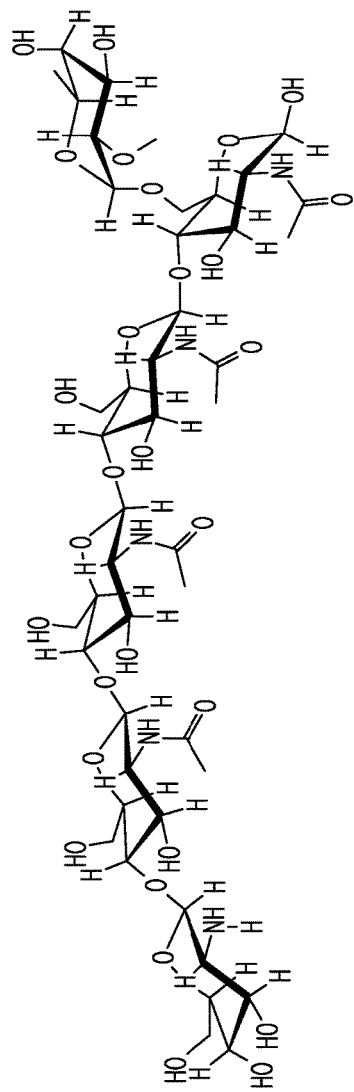
FIGS. 1a and 2a show the chemical structures of chitooligosaccharide compounds (CO's) useful in the practice of the present invention.
Figure 1B:
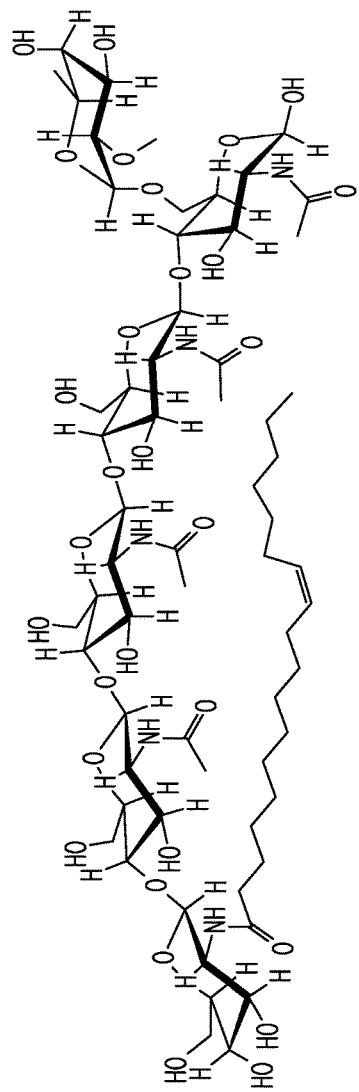
FIGS. 1b and 2b show the chemical structures of the lipo-chitooligosaccharide compounds (LCO's) that correspond to the CO's in FIGS. 1a and 2a, and which are also useful in the practice of the present invention.
Figure 2A:
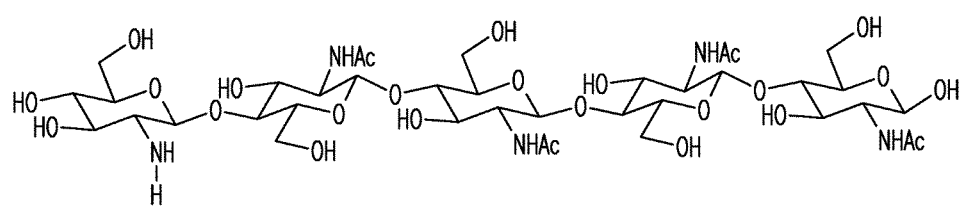
Figure 2B:
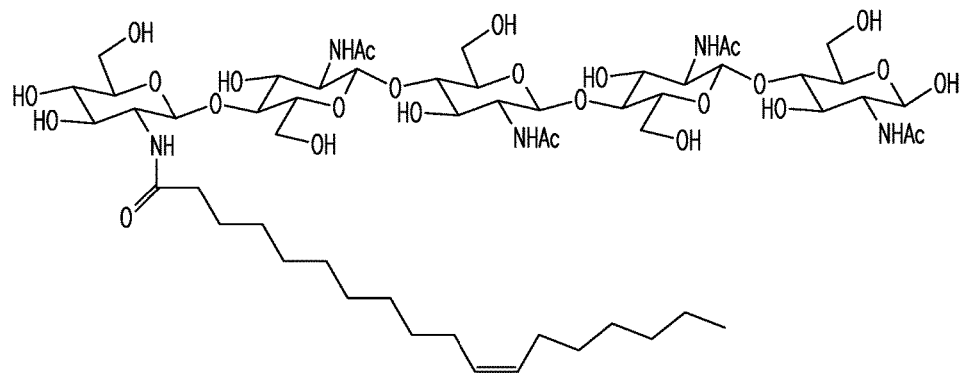

Two CO's suitable for use in the present invention are illustrated in FIGS. 1a and 2a. They correspond to LCO's produced by Bradyrhizobium japonicum and Rhizobium leguminosarum biovar viciae which interact symbiotically with soybean and pea, respectively, but lack the fatty acid chains. The corresponding LCO's produced by these rhizobia (and which are also useful in the practice of the present invention) are illustrated in FIGS. 1b and 2b.

Figure 3A:
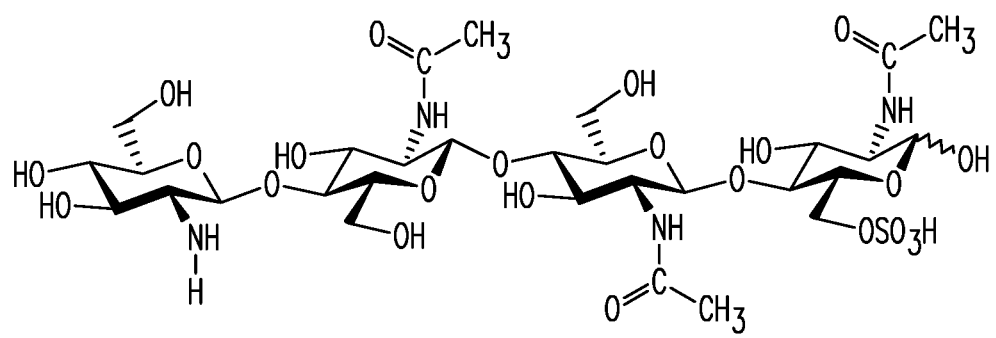
FIGS. 3a and 4a show the chemical structures of other CO's useful in the practice of the present invention.
Figure 3B:
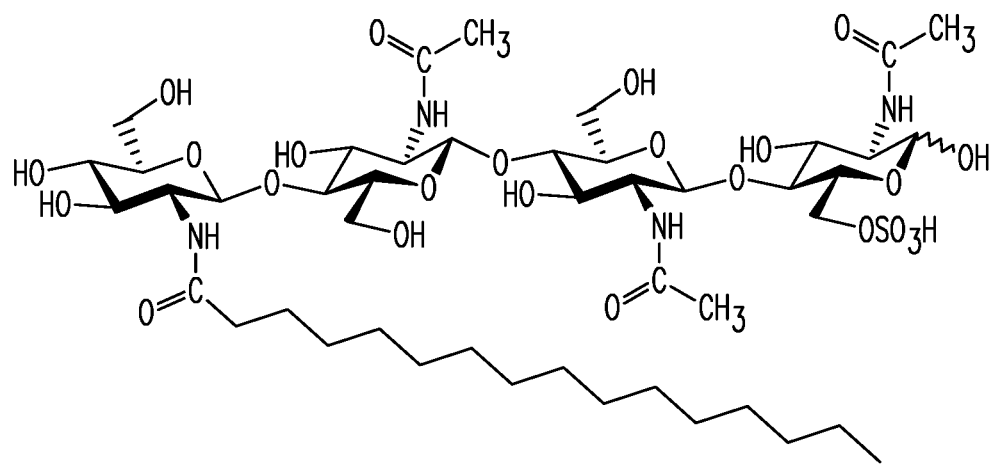
FIGS. 3b and 4b show the chemical structures of the Myc-factors that correspond to the CO's in FIGS. 3a and 3b, and which are also useful in the practice of the present invention.
Figure 4A:
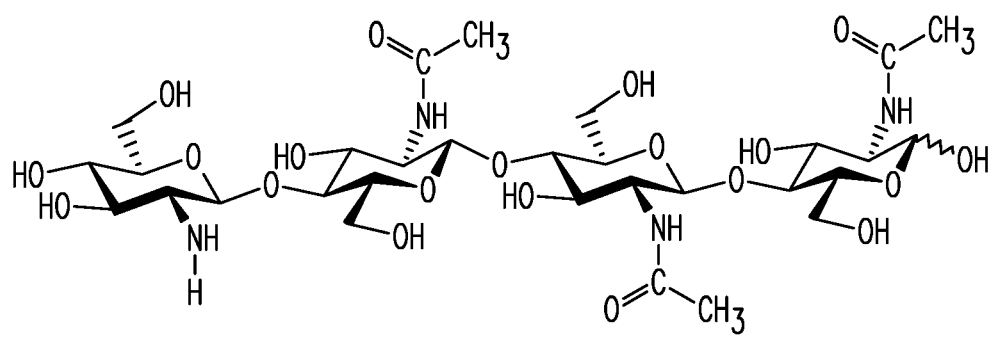
Figure 4B:
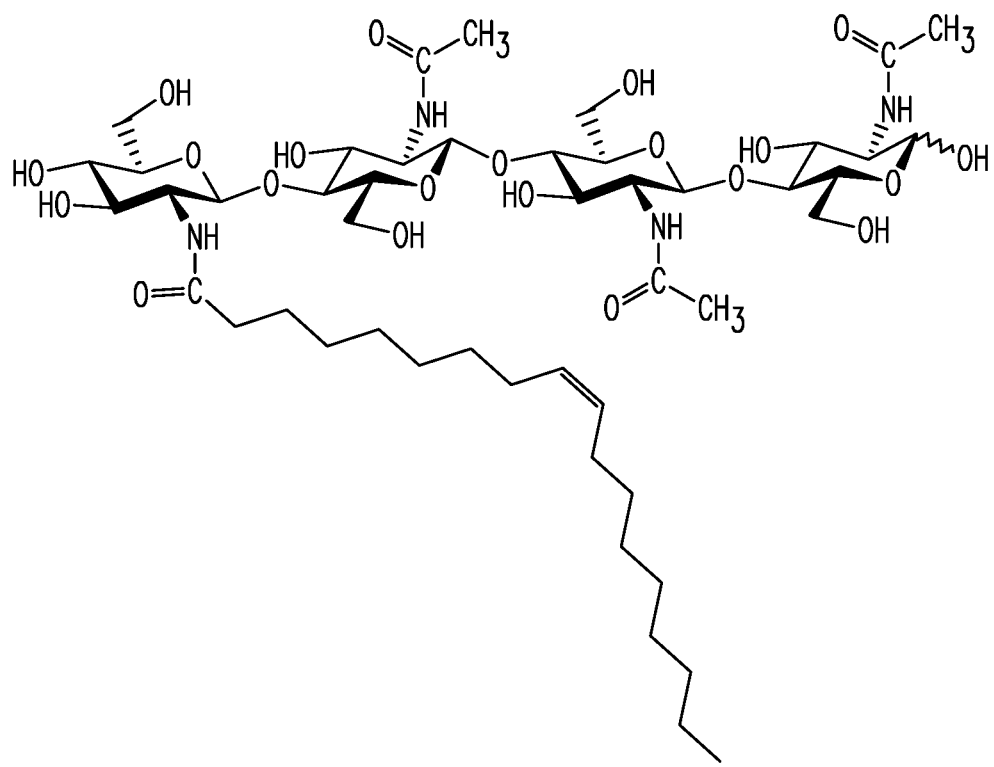

The structures of yet other CO's that may be suitable for use in the practice of the present invention are easily derivable from LCOs obtained (i.e., isolated and/or purified) from a mycorrhizal fungi, such as fungi of the group Glomerocycota, e.g., Glomus intraradices. See, e.g., WO 2010/049751 and Maillet, et al., Nature 469:58-63 (2011) (the LCOs described therein also referred to as "Myc factors"). Representative mycorrhizal fungi-derived CO's are represented by the following structure:

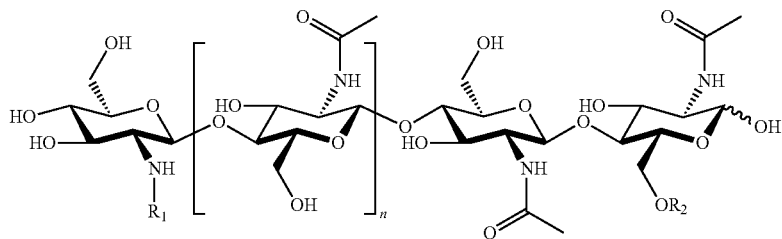

wherein n=1 or 2; $R_1$ represents hydrogen or methyl; and $R_2$ represents hydrogen or $SO_3H$. Two other CO's suitable for use in the present invention, one of which is sulfated, and the other being non-sulfated, are illustrated in FIGS. 3a and 4a respectively. They correspond to two different LCO's produced by the mycorrhizal fungi *Glomas intraradices* which are illustrated in FIGS. 3b and 4b (and which are also useful in the practice of the present invention).

The COs may be synthetic or recombinant. Methods for preparation of synthetic CO's are described, for example, in Robina, supra., Methods for producing recombinant CO's e.g., using *E. coli* as a host, are known in the art. See, e.g., Dumon, et al., ChemBioChem 7:359-65 (2006), Samain, et al., Carbohydrate Res. 302:35-42 (1997); Cottaz, et al., Meth. Eng. 7(4):311-7 (2005) and Samain, et al., J. Biotechnol. 72:33-47 (1999) (e.g., FIG. 1 therein which shows structures of CO's that can be made recombinantly in *E. coli* harboring different combinations of genes nodBCHL). For purposes of the present invention, the at least one CO is structurally distinct from chitins, chitosans, and other chitooligosaccharides made enzymatically using chitin as a starting material.

For the purposes of the present invention, the at least one recombinant CO is at least 60% pure, e.g., at least 60% pure, at least 65% pure, at least 70% pure, at least 75% pure, at least 80% pure, at least 85% pure, at least 90% pure, at least 91% pure, at least 92% pure, at least 93% pure, at least 94% pure, at least 95% pure, at least 96% pure, at least 97% pure, at least 98% pure, at least 99% pure, up to 100% pure.

Seeds may be treated with the at least one CO in several ways such as spraying or dripping. Spray and drip treatment may be conducted by formulating an effective amount of the at least one CO in an agriculturally acceptable carrier, typically aqueous in nature, and spraying or dripping the composition onto seed via a continuous treating system (which is calibrated to apply treatment at a predefined rate in proportion to the continuous flow of seed), such as a drum-type of treater. These methods advantageously employ relatively small volumes of carrier so as to allow for relatively fast drying of the treated seed. In this fashion, large volumes of seed can be efficiently treated. Batch systems, in which a predetermined batch size of seed and signal molecule compositions are delivered into a mixer, may also be employed. Systems and apparatus for performing these processes are commercially available from numerous suppliers, e.g., Bayer CropScience (Gustafson).

In another embodiment, the treatment entails coating seeds with the at least one CO. One such process involves coating the inside wall of a round container with the composition, adding seeds, then rotating the container to cause the seeds to contact the wall and the composition, a process known in the art as "container coating". Seeds can be coated by combinations of coating methods. Soaking typically entails use of an aqueous solution containing the plant growth enhancing agent. For example, seeds can be soaked for about 1 minute to about 24 hours (e.g., for at least 1 min, 5 min, 10 min, 20 min, 40 min, 80 min, 3 hr, 6 hr, 12 hr, 24 hr). Some types of seeds (e.g., soybean seeds) tend to be sensitive to moisture. Thus, soaking such seeds for an extended period of time may not be desirable, in which case the soaking is typically carried out for about 1 minute to about 20 minutes.

In those embodiments that entail storage of seed after application of the at least one CO, adherence of the CO to the seed over any portion of time of the storage period is not critical. Without intending to be bound by any particular theory of operation, Applicants believe that even to the extent that the treating may not cause the plant signal molecule to remain in contact with the seed surface after treatment and during any part of storage, the CO may achieve its intended effect by a phenomenon known as seed memory or seed perception. See, Macchiavelli, et al., J. Exp. Bot. 55(408):1635-40 (2004). Applicants also believe that following treatment the CO diffuses toward the young developing radicle and activates symbiotic and developmental genes which results in a change in the root architecture of the plant. Notwithstanding, to the extent desirable, the compositions containing the CO may further contain a sticking or coating agent. For aesthetic purposes, the compositions may further contain a coating polymer and/or a colorant.

The amount of the at least one CO is effective to enhance growth such that upon harvesting the plant exhibits at least one of increased plant yield measured in terms of bushels/acre, increased root number, increased root length, increased root mass, increased root volume and increased leaf area, compared to untreated plants or plants harvested from untreated seed (with either active). The effective amount of the at least one CO used to treat the seed, expressed in units of concentration, generally ranges from about $10^{-5}$ to about $10^{-14}$ M (molar concentration), and in some embodiments, from about $10^{-5}$ to about $10^{-11}$ M, and in some other embodiments from about $10^{-7}$ to about $10^{-8}$ M. Expressed in units of weight, the effective amount generally ranges from about 1 to about 400 μg/hundred weight (cwt) seed, and in some embodiments from about 2 to about 70 μg/cwt, and in some other embodiments, from about 2.5 to about 3.0 μg/cwt seed.

For purposes of treatment of seed indirectly, i.e., in-furrow treatment, the effective amount of the at least one CO generally ranges from about 1 μg/acre to about 70 μg/acre, and in some embodiments, from about 50 μg/acre to about 60 μg/acre. For purposes of application to the plants, the effective amount of the CO generally ranges from about 1 μg/acre to about 30 μg/acre, and in some embodiments, from about 11 μg/acre to about 20 μg/acre.

Seed may be treated with the at least one CO just prior to or at the time of planting. Treatment at the time of planting may include direct application to the seed as described above, or in some other embodiments, by introducing the actives into the soil, known in the art as in-furrow treatment. In those embodiments that entail treatment of seed followed by storage, the seed may be then packaged, e.g., in 50-lb or 100-lb bags, or bulk bags or containers, in accordance with standard techniques. The seed may be stored for at least 1, 2, 3, 4, 5, 6, 7, 8, 9, 10, 11, or 12 months, and even longer, e.g., 13, 14, 15, 16, 17, 18, 19, 20, 21, 22, 23, 24, 25, 26, 27, 28, 29, 30, 31, 32, 33, 34, 35, 36 months, or even longer, under appropriate storage conditions which are known in the art. Whereas soybean seed may have to be planted the following season, corn seed can be stored for much longer periods of time including upwards of 3 years.

Other Agronomically Beneficial Agents

The present invention may further include treatment of the seed or the plants that germinate from the seed with at least one agriculturally/agronomically beneficial agent. As used herein and in the art, the term "agriculturally or agronomically beneficial" refers to agents that when applied to seeds or plants results in enhancement (which may be statistically significant) of plant characteristics such as plant stand, growth (e.g., as defined in connection with CO's), or vigor in comparison to non-treated seeds or plants. These agents may be formulated together with the at least one CO or applied to the seed or plant via a separate formulation. Representative examples of such agents that may be useful in the practice of the present invention include micronutrients (e.g., vitamins and trace minerals), fatty acids and derivatives thereof, plant signal molecules (other than CO's), herbicides, fungicides and insecticides, phosphate-solubilizing microorganisms, diazotrophs (Rhizobial inoculants), and/or mycorrhizal fungi.

Micronutrients

Representative vitamins that may be useful in the practice of the present invention include calcium pantothenate, folic acid, biotin, and vitamin C. Representative examples of trace minerals that may be useful in the practice of the present invention include boron, chlorine, manganese, iron, zinc, copper, molybdenum, nickel, selenium and sodium.

The amount of the at least one micronutrient used to treat the seed, expressed in units of concentration, generally ranges from 10 ppm to 100 ppm, and in some embodiments, from about 2 ppm to about 100 ppm. Expressed in units of weight, the effective amount generally ranges in one embodiment from about 180 μg to about 9 mg/hundred weight (cwt) seed, and in some embodiments from about 4 μg to about 200 μg/plant when applied on foliage. In other words, for purposes of treatment of seed the effective amount of the at least one micronutrient generally ranges from 30 μg/acre to about 1.5 mg/acre, and in some embodiments, from about 120 mg/acre to about 6 g/acre when applied foliarly.

Fatty Acids

Representative fatty acids that may be useful in the practice of the present invention include the fatty acids that are substituents on naturally occurring LCO's, such as stearic and palmitic acids. Other fatty acids that may be useful include saturated C12-18 fatty acids which (aside from palmitic and stearic acids) include lauric acid, and myristic acid, and unsaturated C12-18 fatty acids such as myristoleic acid, palmitoleic acid, sapienic acid, oleic acid, elaidic acid, vaccenic acid, linoleic acid, linolenic acid, and linoelaidic acid. Linoleic acid and linolenic acid are produced in the course of the biosynthesis of jasmonic acid (which as described below, is also an agronomically beneficial agent for purposes of the present invention). Linoleic acid and linoleic acid (and their derivatives) are reported to be inducers of nod gene expression or LCO production by rhizobacteria. See, e.g., Mabood, Fazli, "Linoleic and linolenic acid induce the expression of nod genes in *Bradyrhizobium japonicum*," USDA 3, May 17, 2001.

Useful derivatives of fatty acids that may be useful in the practice of the present invention include esters, amides, glycosides and salts. Representative esters are compounds in which the carboxyl group of the fatty acid, e.g., linoleic acid and linolenic acid, has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of the fatty acid, e.g., linoleic acid and linolenic acid, has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of fatty acids, e.g., linoleic acid and linolenic acid, include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of the fatty acid with a solution of the base. The salt may be precipitated from solution and be collected by filtration or may be recovered by other means such as by evaporation of the solvent.

The amounts of the fatty acid or derivative thereof are typically between about 10% to about 30%, and in some embodiments about 25% of the amount of the at least one CO.

Plant Signal Molecules

The present invention may also include treatment of seed or plant with a plant signal molecule other than a CO. For purposes of the present invention, the term "plant signal molecule", which may be used interchangeably with "plant growth-enhancing agent" broadly refers to any agent, both naturally occurring in plants or microbes, and synthetic (and which may be non-naturally occurring) that directly or indirectly activates a plant biochemical pathway, resulting in increased plant growth, measureable at least in terms of at least one of increased yield measured in terms of bushels/acre, increased root number, increased root length, increased root mass, increased root volume and increased leaf area, compared to untreated plants or plants harvested from untreated seed. Representative examples of plant signal molecules that may be useful in the practice of the present invention include lipo-chitooligosaccharides, chitinous compounds (other than COs), flavonoids, jasmonic acid, linoleic acid and linolenic acid and their derivatives (supra), and karrikins.

Lipo-chitooligosaccharide compounds (LCO's), also known in the art as symbiotic Nod signals or Nod factors, consist of an oligosaccharide backbone of β-1,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. See, e.g., Denarie, et al., Ann. Rev. Biochem. 65:503-35 (1996), Hamel, et al., supra., Prome, et al., Pure & Appl. Chem. 70(1):55-60 (1998). An example of an LCO is presented below as formula I

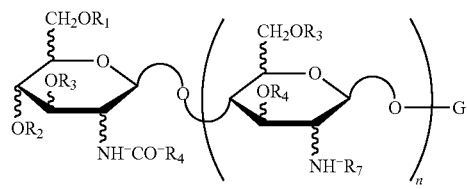

in which:
G is a hexosamine which can be substituted, for example, by an acetyl group on the nitrogen, a sulfate group, an acetyl group and/or an ether group on an oxygen,
$R_1$, $R_2$, $R_3$, $R_5$, $R_6$ and $R_7$, which may be identical or different, represent H, $CH_3CO$—, $C_xH_yCO$— where x is an integer between 0 and 17, and y is an integer between 1 and 35, or any other acyl group such as for example a carbamoyl,
$R_4$ represents a mono-, di- or triunsaturated aliphatic chain containing at least 12 carbon atoms, and n is an integer between 1 and 4.

LCOs may be obtained (isolated and/or purified) from bacteria such as Rhizobia, e.g., Rhizobium sp., Bradyrhizobium sp., Sinorhizobium sp. and Azorhizobium sp. LCO structure is characteristic for each such bacterial species, and each strain may produce multiple LCO's with different structures. For example, specific LCOs from S. meliloti have also been described in U.S. Pat. No. 5,549,718 as having the formula II:

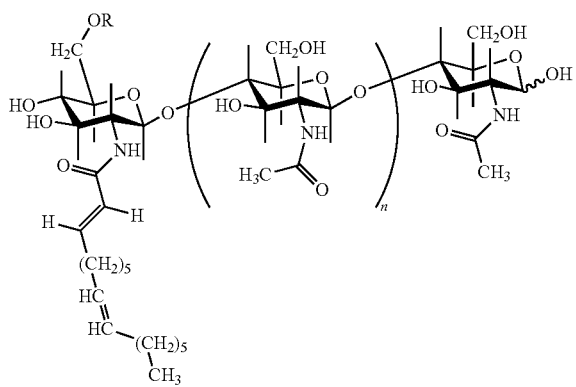

in which R represents H or $CH_3CO$— and n is equal to 2 or 3.

Even more specific LCOs include NodRM, NodRM-1, NodRM-3. When acetylated (the R=$CH_3CO$—), they become AcNodRM-1, and AcNodRM-3, respectively (U.S. Pat. No. 5,545,718).

LCOs from Bradyrhizobium japonicum are described in U.S. Pat. Nos. 5,175,149 and 5,321,011. Broadly, they are pentasaccharide phytohormones comprising methylfucose. A number of these B. japonicum-derived LCOs are described: BjNod-V ($C_{18:1}$); BjNod-V ($A_C$, $C_{18:1}$), BjNod-V ($C_{16:1}$); and BjNod-V ($A_C$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

LCO's used in embodiments of the invention may be obtained (i.e., isolated and/or purified) from bacterial strains that produce LCO's, such as strains of Azorhizobium, Bradyrhizobium (including B. japonicum), Mesorhizobium, Rhizobium (including R. leguminosarum), Sinorhizobium (including S. meliloti), and bacterial strains genetically engineered to produce LCO's.

LCO's are the primary determinants of host specificity in legume symbiosis (Diaz, et al., Mol. Plant-Microbe Interactions 13:268-276 (2000)). Thus, within the legume family, specific genera and species of rhizobia develop a symbiotic nitrogen-fixing relationship with a specific legume host. These plant-host/bacteria combinations are described in Hungria, et al., Soil Biol. Biochem. 29:819-830 (1997), Examples of these bacteria/legume symbiotic partnerships include S. meliloti/alfalfa and sweet clover; R. leguminosarum biovar viciae/peas and lentils; R. leguminosarum biovar phaseoli/beans; Bradyrhizobium japonicum/soybeans; and R. leguminosarum biovar trifolii/red clover. Hungria also lists the effective flavonoid Nod gene inducers of the rhizobial species, and the specific LCO structures that are produced by the different rhizobial species. However, LCO specificity is only required to establish nodulation in legumes. In the practice of the present invention, use of a given LCO is not limited to treatment of seed of its symbiotic legume partner, in order to achieve increased plant yield measured in terms of bushels/acre, increased root number, increased root length, increased root mass, increased root volume and increased leaf area, compared to plants harvested from untreated seed, or compared to plants harvested from seed treated with the signal molecule just prior to or within a week or less of planting.

Thus, by way of further examples, LCO's and non-naturally occurring derivatives thereof that may be useful in the practice of the present invention are represented by the following formula:

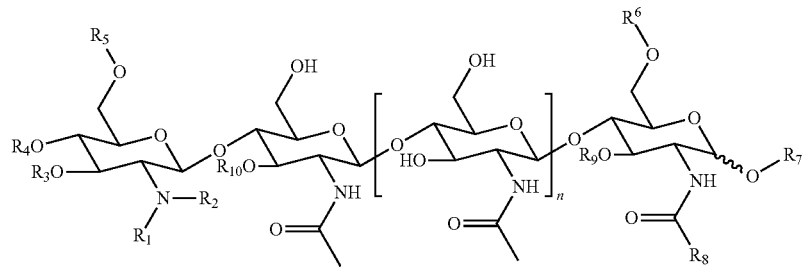

wherein $R_1$ represents C14:0, 3OH—C14:0, iso-C15:0, C16:0, 3-OH—C16:0, iso-C15:0, C16:1, C16:2, C16:3, iso-C17:0, iso-C17:1, C18:0, 3OH—C18:0, C18:0/3-OH, C18:1, OH—C18:1, C18:2, C18:3, C18:4, C19:1 carbamoyl, C20:0, C20:1, 3-OH—C20:1, C20:1/3-OH, C20:2, C20:3, C22:1, and C18-26(ω-1)-OH (which according to D'Haeze, et al., supra, includes C18, C20, C22, C24 and C26 hydroxylated species and C16:1Δ9, C16:2 (Δ2,9) and C16:3 (Δ2,4,9)); $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc, and 4-0-AcFuc; $R_7$ represents hydrogen, mannosyl or glycerol; $R_8$ represents hydrogen, methyl, or —CH$_2$OH; $R_9$ represents hydrogen, arabinosyl, or fucosyl; $R_{10}$ represents hydrogen, acetyl or fucosyl; and n represents 0, 1, 2 or 3. The structures of the naturally occurring Rhizobial LCO's embraced by this structure are described in D'Haeze, et al., supra.

By way of even further additional examples, an LCO obtained from B. japonicum, illustrated in FIG. 1b, may be used to treat leguminous seed other than soybean and non-leguminous seed such as corn. As another example, the LCO obtainable from R. leguminosarum illustrated in FIG. 2b (designated LCO-V (C18:1), SP104) can be used to treat leguminous seed other than pea and non-legumes too.

Also encompassed by the present invention is use of LCOs obtained (i.e., isolated and/or purified) from a mycorrhizal fungi, such as fungi of the group Glomerocycota, e.g., Glomus intraradices. The structures of representative LCOs obtained from these fungi are described in WO 2010/049751 and WO 2010/049751 (the LCOs described therein also referred to as "Myc factors"). Representative mycorrhizal fungi-derived CO's and non-naturally occurring derivatives thereof are represented by the following structure:

Further encompassed by the present invention is use of synthetic LCO compounds, such as those described in WO 2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze, et al., Glycobiology 12:79R-105R (2002). Precursor oligosaccharide molecules (COs, which as described below, are also useful as plant signal molecules in the present invention) for the construction of LCOs may also be synthesized by genetically engineered organisms, e.g., as described in Samain, et al., Carbohydrate Res. 302:35-42 (1997); Cottaz, et al., Meth. Eng. 7(4):311-7 (2005) and Samain, et al., J. Biotechnol. 72:33-47 (1999) (e.g., FIG. 1 therein which shows structures of LCO's that can be made recombinantly in E. coli harboring different combinations of genes nodBCHL).

LCO's may be utilized in various forms of purity and may be used alone or in the form of a culture of LCO-producing bacteria or fungi. For example, OPTIMIZE® (commercially available from Novozymes BioAg Limited) contains a culture of B. japonicum that produces an LCO (LCO-V(C18:1, MeFuc), MOR116) that is illustrated in FIG. 1b Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage. Chitooligosaccharides (COs) as described above, may be used as starting materials for the

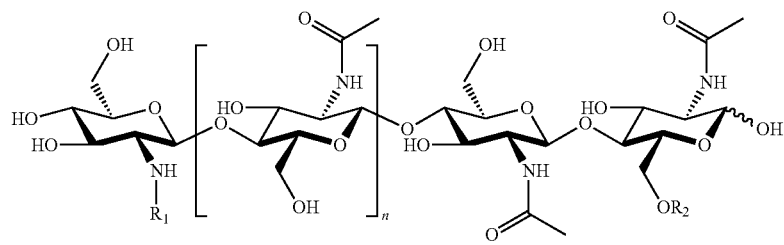

wherein n=1 or 2; $R_1$ represents C16, C16:0, C16:1, C16:2, C18:0, C18:1Δ9Z or C18:1Δ11Z; and $R_2$ represents hydrogen or SO$_3$H. In some embodiments, the LCO's are produced by the mycorrhizal fungi which are illustrated in FIGS. 3b and 4b.

production of synthetic LCOs. For the purposes of the present invention, recombinant LCO's are at least 60% pure, e.g., at least 60% pure, at least 65% pure, at least 70% pure, at least 75% pure, at least 80% pure, at least 85% pure, at least 90% pure, at least 91% pure, at least 92% pure, at least 93% pure, at least 94% pure, at least 95% pure, at least 96% pure, at least 97% pure, at least 98% pure, at least 99% pure, up to 100% pure.

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4,5-dihydroxy-6-(hydroxymethyl)oxan-2yl]methoxymethyl]-2-[[5-acetylamino-4, 6-dihydroxy-2-(hydroxy methyl)oxan-3-yl]methoxymethyl]-4-hydroxy-6-(hydroxymethyl)oxan-3-ys]ethanamide), and chitosan, (IUPAC: 5-amino-6-[5-amino-6-[5-amino-4,6-dihydroxy-2 (hydroxymethyl)oxan-3-yl]oxy-4-hydroxy-2-(hydroxymethyl)oxan-3-yl]oxy-2(hydroxymethyl)oxane-3,4-diol).
These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich, et al., Lett. Appl. Microbiol. 35:17-21 (2002) (preparation from fungal cell walls), and U.S. Pat. No. 5,965,545 (preparation from crab shells and hydrolysis of commercial chitosan). See, also, Jung, et al., Carbohydrate Polymers 67:256-59 (2007); Khan, et al., Photosynthetica 40(4):621-4 (2002). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 OkD; and high molecular weight chitosan of up to 70 OkD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include chalcones, anthocyanidins, coumarins, flavones, flavanols, flavonols, flavanones, and isoflavones. See, Jain, et al., J. Plant Biochem. & Biotechnol. 11:1-10 (2002); Shaw, et al., Environmental Microbiol. 11:1867-80 (2006).

Representative flavonoids that may be useful in the practice of the present invention include genistein, daidzein, formononetin, naringenin, hesperetin, luteolin, and apigenin. Flavonoid compounds are commercially available, e.g., from Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston, et al., Plant Physiology 137:1375-88 (2005).

Jasmonic acid (JA, [1R-[1α,2β(Z)]]-3-oxo-2-(pentenyl) cyclopentaneacetic acid) and its derivatives (which include linoleic acid and linolenic acid (which are described above in connection with fatty acids and their derivatives), may be used in the practice of the present invention. Jasmonic acid and its methyl ester, methyl jasmonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibberella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Like linoleic acid and linolenic acid, jasmonates (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001.

Useful derivatives of jasmonic acid that may be useful in the practice of the present invention include esters, amides, glycosides and salts. Representative esters are compounds in which the carboxyl group of jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikins are vinylogous 4H-pyrones e.g., 2H-furo[2,3-c]pyran-2-ones including derivatives and analogues thereof. Examples of these compounds are represented by the following structure:

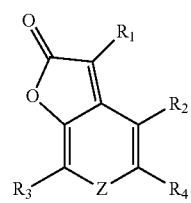

wherein; Z is O, S or NR$_5$; R$_1$, R$_2$, R$_3$, and R$_4$ are each independently H, alkyl, alkenyl, alkynyl, phenyl, benzyl, hydroxy, hydroxyalkyl, alkoxy, phenyloxy, benzyloxy, CN, COR$_E$, COOR=, halogen, NR$_6$R$_7$, or NO$_2$; and R$_5$, R$_6$, and R$_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present invention include the following: 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R$_4$=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH$_3$), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H), 3,6-dimethylfuro[2,3-c]pyridin-2(6H)-one (where Z=N—CH$_3$, R$_1$=CH$_3$, R$_2$, R$_3$, R$_4$=H). See, U.S. Pat. No. 7,576,213. These molecules are also known as karrikins. See, Halford, supra.

The amount of the at least one plant signal molecule used to treat the seed, expressed in units of concentration, generally ranges from about $10^{-8}$ to about $10^{-14}$ M (molar concentration), and in some embodiments, from about $10^{-8}$ to about $10^{-11}$ M, and in some other embodiments from about $10^{-7}$ to about $10^{-8}$ M. Expressed in units of weight, the effective amount generally ranges from about 1 to about 400 μg/hundred weight (cwt) seed, and in some embodiments from about 2 to about 70 μg/cwt, and in some other embodiments, from about 2.5 to about 3.0 μg/cwt seed.

For purposes of treatment of seed indirectly, i.e., in-furrow treatment, the effective amount of the at least one plant signal molecule generally ranges from 1 μg/acre to about 70 μg/acre, and in some embodiments, from about 50 μg/acre to about 60 μg/acre. For purposes of application to the plants, the effective amount of the at least one plant signal molecule generally ranges from 1 μg/acre to about 30 μg/acre, and in some embodiments, from about 11 μg/acre to about 20 μg/acre.

Herbicides, Fungicides and Insecticides

Suitable herbicides include bentazon, acifluorfen, chlorimuron, lactofen, clomazone, fluazifop, glufosinate, glyphosate, sethoxydim, imazethapyr, imazamox, fomesafe, flumiclorac, imazaquin, and clethodim. Commercial products containing each of these compounds are readily available. Herbicide concentration in the composition will generally correspond to the labeled use rate for a particular herbicide.

A "fungicide" as used herein and in the art, is an agent that kills or inhibits fungal growth. As used herein, a fungicide "exhibits activity against" a particular species of fungi if treatment with the fungicide results in killing or growth inhibition of a fungal population (e.g., in the soil) relative to an untreated population. Effective fungicides in accordance with the invention will suitably exhibit activity against a broad range of pathogens, including but not limited to *Phytophthora*, *Rhizoctonia*, *Fusarium*, *Pythium*, *Phomopsis* or *Selerotinia* and *Phakopsora* and combinations thereof.

Commercial fungicides may be suitable for use in the present invention. Suitable commercially available fungicides include PROTEGE, RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAPTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides are most suitably used in accordance with the manufacturer's instructions at the recommended concentrations.

As used herein, an insecticide "exhibits activity against" a particular species of insect if treatment with the insecticide results in killing or inhibition of an insect population relative to an untreated population. Effective insecticides in accordance with the invention will suitably exhibit activity against a broad range of insects including, but not limited to, wireworms, cutworms, grubs, corn rootworm, seed corn maggots, flea beetles, chinch bugs, aphids, leaf beetles, and stink bugs.

Commercial insecticides may be suitable for use in the present invention. Suitable commercially-available insecticides include CRUISER (Syngenta, Wilmington, Del.), GAUCHO and PONCHO (Gustafson, Plano, Tex.). Active ingredients in these and other commercial insecticides include thiamethoxam, clothianidin, and imidacloprid. Commercial insecticides are most suitably used in accordance with the manufacturer's instructions at the recommended concentrations.

Phosphate Solubilizing Microorganisms, Diazotrophs (Rhizobial Inoculants), and/or Mycorrhizal Fungi The present invention may further include treatment of the seed with a phosphate solubilizing microorganism. As used herein, "phosphate solubilizing microorganism" is a microorganism that is able to increase the amount of phosphorous available for a plant. Phosphate solubilizing microorganisms include fungal and bacterial strains. In embodiment, the phosphate solubilizing microorganism is a spore forming microorganism.

Non-limiting examples of phosphate solubilizing microorganisms include species from a genus selected from the group consisting of *Acinetobacter*, *Arthrobacter*, *Arthrobotrys*, *Aspergillus*, *Azospirillum*, *Bacillus*, *Burkholderia*, *Candida* *Chryseomonas*, *Enterobacter*, *Eupenicillium*, *Exiguobacterium*, *Klebsiella*, *Kluyvera*, *Microbacterium*, *Mucor*, *Paecilomyces*, *Paenibacillus*, *Penicillium*, *Pseudomonas*, *Serratia*, *Stenotrophomonas*, *Streptomyces*, *Streptosporangium*, *Swaminathania*, *Thiobacillus*, *Torulospora*, *Vibrio*, *Xanthobacter*, and *Xanthomonas*.

Non-limiting examples of phosphate solubilizing microorganisms are selected from the group consisting *Acinetobacter calcoaceticus*, *Acinetobacter sp*, *Arthrobacter* sp., *Arthrobotrys oligospora*, *Aspergillus niger*, *Aspergillus* sp., *Azospirillum halopraeferans*, *Bacillus amyloliquefaciens*, *Bacillus atrophaeus*, *Bacillus circulans*, *Bacillus licheniformis*, *Bacillus subtilis*, *Burkholderia cepacia*, *Burkholderia vietnamiensis*, *Candida krissii*, *Chryseomonas luteola*, *Enterobacter aerogenes*, *Enterobacter asburiae*, *Enterobacter* sp., *Enterobacter taylorae*, *Eupenicillium parvum*,

*Exiguobacterium* sp., *Klebsiella* sp., *Kluyvera cryocrescens*, *Microbacterium* sp., *Mucor ramosissimus*, *Paecilomyces hepialid*, *Paecilomyces marquandii*, *Paenibacillus macerans*, *Paenibacillus mucilaginosus*, *Pantoea aglomerans*, *Penicillium expansum*, *Pseudomonas corrugate*, *Pseudomonas fluorescens*, *Pseudomonas lutea*, *Pseudomonas poae*, *Pseudomonas putida*, *Pseudomonas stutzeri*, *Pseudomonas trivialis*, *Serratia marcescens*, *Stenotrophomonas maltophilia*, *Streptomyces* sp., *Streptosporangium* sp., *Swaminathania salitolerans*, *Thiobacillus ferrooxidans*, *Torulospora globosa*, *Vibrio proteolyticus*, *Xanthobacter agilis*, and *Xanthomonas campestris*

In a particular embodiment, the phosphate solubilizing microorganism is a strain of the fungus *Penicillium*. Strains of the fungus *Penicillium* that may be useful in the practice of the present invention include *P. bilaiae* (formerly known as *P. bilaii*), *P. albidum*, *P. aurantiogriseum*, *P. chrysogenum*, *P. citreonigrum*, *P. citrinum*, *P. digitatum*, *P. frequentas*, *P. fuscum*, *P. gaestrivorus*, *P. glabrum*, *P. griseofulvum*, *P. implicatum*, *P. janthinellum*, *P. lilacinum*, *P. minioluteum*, *P. montanense*, *P. nigricans*, *P. oxalicum*, *P. pinetorum*, *P. pinophilum*, *P. purpurogenum*, *P. radicans*, *P. radicum*, *P. raistrickii*, *P. rugulosum*, *P. simplicissimum*, *P. solitum*, *P. variabile*, *P. velutinum*, *P. viridicatum*, *P. glaucum*, *P. fussiporus*, and *P. expansum*.

In one particular embodiment, the *Penicillium* species is *P. bilaiae*. In another particular embodiment the *P. bilaiae* strains are selected from the group consisting of ATCC 20851, NRRL 50169, ATCC 22348, ATCC 18309, NRRL 50162 (Wakelin, et al., 2004. Biol Fertil Soils 40:36-43). In another particular embodiment the *Penicillium* species is *P. gaestrivorus*, e.g., NRRL 50170 (see, Wakelin, supra.).

In some embodiments, more than one phosphate solubilizing microorganism is used, such as, at least two, at least three, at least four, at least five, at least 6, including any combination of the *Acinetobacter*, *Arthrobacter*, *Arthrobotrys*, *Aspergillus*, *Azospirillum*, *Bacillus*, *Burkholderia*, *Candida*, *Chryseomonas*, *Enterobacter*, *Eupenicillium*, *Exiguobacterium*, *Klebsiella*, *Kluyvera*, *Microbacterium*, *Mucor*, *Paecilomyces*, *Paenibacillus*, *Penicillium*, *Pseudomonas*, *Serratia*, *Stenotrophomonas*, *Streptomyces*, *Streptosporangium*, *Swaminathania*, *Thiobacillus*, *Torulospora*, *Vibrio*, *Xanthobacter*, and *Xanthomonas*, including one species selected from the following group: *Acinetobacter calcoaceticus*, *Acinetobacter* sp, *Arthrobacter* sp., *Arthrobotrys oligospora*, *Aspergillus niger*, *Aspergillus* sp., *Azospirillum halopraeferans*, *Bacillus amyloliquefaciens*, *Bacillus atrophaeus*, *Bacillus circulans*, *Bacillus licheniformis*, *Bacillus subtilis*, *Burkholderia cepacia*, *Burkholderia vietnamiensis*, *Candida krissii*, *Chryseomonas luteola*, *Enterobacter aerogenes*, *Enterobacter asburiae*, *Enterobacter* sp., *Enterobacter taylorae*, *Eupenicillium parvum*, *Exiguobacterium* sp., *Klebsiella* sp., *Kluyvera cryocrescens*, *Microbacterium* sp., *Mucor ramosissimus*, *Paecilomyces hepialid*, *Paecilomyces marquandii*, *Paenibacillus macerans*, *Paenibacillus mucilaginosus*, *Pantoea aglomerans*, *Penicillium expansum*, *Pseudomonas corrugate*, *Pseudomonas fluorescens*, *Pseudomonas lutea*, *Pseudomonas poae*, *Pseudomonas putida*, *Pseudomonas stutzeri*, *Pseudomonas trivialis*, *Serratia marcescens*, *Stenotrophomonas maltophilia*, *Streptomyces* sp., *Streptosporangium* sp., *Swaminathania salitolerans*, *Thiobacillus ferrooxidans*, *Torulospora globosa*, *Vibrio proteolyticus*, *Xanthobacter agilis*, and *Xanthomonas campestris*

In some embodiments, two different strains of the same species may also be combined, for example, at least two different strains of *Penicillium* are used. The use of a combination of at least two different *Penicillium* strains has the following advantages. When applied to soil already containing insoluble (or sparingly soluble) phosphates, the use of the combined fungal strains will result in an increase in the amount of phosphorus available for plant uptake compared to the use of only one *Penicillium* strain. This in turn may result in an increase in phosphate uptake and/or an increase in yield of plants grown in the soil compared to use of individual strains alone. The combination of strains also enables insoluble rock phosphates to be used as an effective fertilizer for soils which have inadequate amounts of available phosphorus. Thus, in some embodiments, one strain of *P. bilaiae* and one strain of *P. gaestrivorus* are used. In other embodiments, the two strains are NRRL 50169 and NRRL 50162. In further embodiments, the at least two strains are NRRL 50169 and NRRL 50170. In yet further embodiments, the at least two strains are NRRL 50162 and NRRL 50170.

The phosphate solubilizing microorganisms may be prepared using any suitable method known to the person skilled in the art, such as, solid state or liquid fermentation using a suitable carbon source. The phosphate solubilizing microorganism is preferably prepared in the form of a stable spore.

In an embodiment, the phosphate solubilizing microorganism is a *Penicillium* fungus. The *Penicillium* fungus according to the invention can be grown using solid state or liquid fermentation and a suitable carbon source. *Penicillium* isolates may be grown using any suitable method known to the person skilled in the art. For example, the fungus may be cultured on a solid growth medium such as potato dextrose agar or malt extract agar, or in flasks containing suitable liquid media such as Czapek-Dox medium or potato dextrose broth. These culture methods may be used in the preparation of an inoculum of *Penicillium* spp. for treating (e.g., coating) seeds and/or application to an agronomically acceptable carrier to be applied to soil. The term "inoculum" as used in this specification is intended to mean any form of phosphate solubilizing microorganism, fungus cells, mycelium or spores, bacterial cells or bacterial spores, which is capable of propagating on or in the soil when the conditions of temperature, moisture, etc., are favorable for fungal growth.

Solid state production of *Penicillium* spores may be achieved by inoculating a solid medium such as a peat or vermiculite-based substrate, or grains including, but not limited to, oats, wheat, barley, or rice. The sterilized medium (achieved through autoclaving or irradiation) is inoculated with a spore suspension ($1 \times 10^2$-$1 \times 10^7$ cfu/ml) of the appropriate *Penicillium* spp. and the moisture adjusted to 20 to 50%, depending on the substrate. The material is incubated for 2 to 8 weeks at room temperature. The spores may also be produced by liquid fermentation (Cunningham et al., 1990. Can J Bot. 68:2270-2274). Liquid production may be achieved by cultivating the fungus in any suitable media, such as potato dextrose broth or sucrose yeast extract media, under appropriate pH and temperature conditions that may be determined in accordance with standard procedures in the art.

The resulting material may be used directly, or the spores may be harvested, concentrated by centrifugation, formulated, and then dried using air drying, freeze drying, or fluid bed drying techniques (Friesen, et al., 2005, Appl. Microbiol. Biotechnol. 68:397-404) to produce a wettable powder. The wettable powder is then suspended in water, applied to the surface of seeds, and allowed to dry prior to planting. The wettable powder may be used in conjunction with other seed treatments, such as, but not limited to, chemical seed treatments, carriers (e.g., talc, clay, kaolin, silica gel, kaolinite) or polymers (e.g., methylcellulose, polyvinylpyrrolidone). Alternatively, a spore suspension of the appropriate *Penicillium* spp. may be applied to a suitable soil-compatible carrier (e.g., peat-based powder or granule) to appropriate final moisture content. The material may be incubated at room temperature, typically for about 1 day to about 8 weeks, prior to use.

Aside from the ingredients used to cultivate the phosphate solubilizing microorganism, including, e.g., ingredients referenced above in the cultivation of *Penicillium*, the phosphate solubilizing microorganism may be formulated using other agronomically acceptable carriers. As used herein in connection with "carrier", the term "agronomically acceptable" refers to any material which can be used to deliver the actives to a seed, soil or plant, and preferably which carrier can be added (to the seed, soil or plant) without having an adverse effect on plant growth, soil structure, soil drainage or the like. Suitable carriers comprise, but are not limited to, wheat chaff, bran, ground wheat straw, peat-based powders or granules, gypsum-based granules, and clays (e.g., kaolin, bentonite, montmorillonite). When spores are added to the soil a granular formulation will be preferable. Formulations as liquid, peat, or wettable powder will be suitable for coating of seeds. When used to coat seeds, the material can be mixed with water, applied to the seeds and allowed to dry. Example of yet other carriers include moistened bran, dried, sieved and applied to seeds prior coated with an adhesive, e.g., gum arabic. In embodiments that entail formulation of the actives in a single composition, the agronomically acceptable carrier may be aqueous.

The amount of the at least one phosphate solubilizing microorganism varies depending on the type of seed or soil, the type of crop plants, the amounts of the source of phosphorus and/or micronutrients present in the soil or added thereto, etc. A suitable amount can be found by simple trial and error experiments for each particular case. Normally, for *Penicillium*, for example, the application amount falls into the range of 0.001-1.0 Kg fungal spores and mycelium (fresh weight) per hectare, or $10^2$-$10^6$ colony forming units (cfu) per seed (when coated seeds are used), or on a granular carrier applying between $1\times10^6$ and $1\times10^{11}$ colony forming units per hectare. The fungal cells in the form of e.g., spores and the carrier can be added to a seed row of the soil at the root level or can be used to coat seeds prior to planting.

In embodiments, for example, that entail use of at least two strains of a phosphate solubilizing microorganism, such as, two strains of *Penicillium*, commercial fertilizers may be added to the soil instead of (or even as well as) natural rock phosphate. The source of phosphorous may contain a source of phosphorous native to the soil. In other embodiments, the source of phosphorous may be added to the soil. In one embodiment the source is rock phosphate. In another embodiment the source is a manufactured fertilizer. Commercially available manufactured phosphate fertilizers are of many types. Some common ones are those containing monoammonium phosphate (MAP), triple super phosphate (TSP), diammonium phosphate, ordinary superphosphate and ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In a further embodiment, the source or phosphorus is organic. An organic fertilizer refers to a soil amendment derived from natural sources that guarantees, at least, the minimum percentages of nitrogen, phosphate, and potash. Examples include plant and animal by-products, rock powders, seaweed, inoculants, and conditioners. Specific representative examples include bone meal, meat meal, animal manure, compost, sewage sludge, or guano.

Other fertilizers, such as nitrogen sources, or other soil amendments may of course also be added to the soil at approximately the same time as the phosphate solubilizing microorganism or at other times, so long as the other materials are not toxic to the fungus.

Diazotrophs are bacteria and archaea that fix atmospheric nitrogen gas into a more usable form such as ammonia. Examples of diazotrophs include bacteria from the genera *Rhizobium* spp. (e.g., *R. cellulosilyticum, R. daejeonense, R. etli, R. galegae, R. gallicum, R. giardinii, R. hainanense, R. huautlense, R. indigoferae, R. leguminosarum, R. loessense, R. lupini, R. lusitanum, R. meliloti, R. mongolense, R. miluonense, R. sullae, R. tropici, R. undicola*, and/or *R. yanglingense*), *Bradyrhizobium* spp. (e.g., *B. bete, B. canariense, B. elkanii, B. iriomotense, B. japonicum, B. jicamae, B. liaoningense, B. pachyrhizi*, and/or *B. yuanmingense*), *Azorhizobium* spp. (e.g., *A. caulinodans* and/or *A. doebereinerae*), *Sinorhizobium* spp. (e.g., *S. abri, S. adhaerens, S. americanum, S. aboris, S. fredii, S. indiaense, S. kostiense, S. kummerowiae, S. medicae, S. meliloti, S. mexicanus, S. morelense, S. saheli, S. terangae*, and/or *S. xinjiangense*), *Mesorhizobium* spp., (*M. albiziae, M. amorphae, M. chacoense, M. ciceri, M. huakuii, M. loti, M. mediterraneum, M. pluifarium, M. septentrionale, M. temperatum*, and/or *M. tianshanense*), and combinations thereof. In a particular embodiment, the diazotroph is selected from the group consisting of *B. japonicum, R leguminosarum, R meliloti, S. meliloti*, and combinations thereof. In another embodiment, the diazotroph is *B. japonicum*. In another embodiment, the diazotroph is *R leguminosarum*. In another embodiment, the diazotroph is *R meliloti*. In another embodiment, the diazotroph is *S. meliloti*.

Mycorrhizal fungi form symbiotic associations with the roots of a vascular plant, and provide, e.g., absorptive capacity for water and mineral nutrients due to the comparatively large surface area of mycelium. Mycorrhizal fungi include endomycorrhizal fungi (also called vesicular arbuscular mycorrhizae, VAMs, arbuscular mycorrhizae, or AMs), an ectomycorrhizal fungi, or a combination thereof. In one embodiment, the mycorrhizal fungi is an endomycorrhizae of the phylum Glomeromycota and genera *Glomus* and *Gigaspora*. In still a further embodiment, the endomycorrhizae is a strain of *Glomus aggregatum, Glomus brasilianum, Glomus clarum, Glomus deserticola, Glomus etunicatum, Glomus fasciculatum, Glomus intraradices, Glomus monosporum*, or *Glomus mosseae, Gigaspora margarita*, or a combination thereof.

Examples of mycorrhizal fungi include ectomycorrhizae of the phylum *Basidiomycota, Ascomycota*, and *Zygomycota*. Other examples include a strain of *Laccaria* bicolor, *Laccaria laccata, Pisolithus tinctorius, Rhizopogon amylopogon, Rhizopogon fulvigleba, Rhizopogon luteolus, Rhizopogon villosuli, Scleroderma cepa, Scleroderma citrinum*, or a combination thereof.

The mycorrhizal fungi include ecroid mycorrhizae, arbutoid mycorrhizae, or monotropoid mycorrhizae. Arbuscular and ectomycorrhizae form ericoid mycorrhiza with many plants belonging to the order Ericales, while some Ericales form arbutoid and monotropoid mycorrhizae. In one embodiment, the mycorrhiza may be an ericoid mycorrhiza, preferably of the phylum Ascomycota, such as *Hymenoscy-* phous ericae or *Oidiodendron* sp. In another embodiment, the mycorrhiza also may be an arbutoid mycorrhiza, preferably of the phylum Basidiomycota. In yet another embodiment, the mycorrhiza may be a monotripoid mycorrhiza, preferably of the phylum Basidiomycota. In still yet another embodiment, the mycorrhiza may be an orchid mycorrhiza, preferably of the genus *Rhizoctonia*.

The methods of the present invention are applicable to leguminous seed, representative examples of which include soybean, alfalfa, peanut, pea, lentil, bean and clover. The methods of the present invention are also applicable to non-leguminous seed, e.g., Poaceae, Cucurbitaceae, Malvaceae, Asteraceae, Chenopodiaceae and Solonaceae. Representative examples of non-leguminous seed include field crops such as corn, rice, oat, rye, barley and wheat, cotton and canola, and vegetable crops such as potatoes, tomatoes, cucumbers, beets, lettuce and cantaloupe.

The invention will now be described in terms of the following non-limiting examples. Unless indicated to the contrary, water was used as the control (indicated as "control" or "CHK").

EXAMPLES 1-17: Greenhouse Experiments

Example 1: In Vitro Tomato Seedling Root Growth Bioassay

Tomato seeds of hybrid tomato var. Royal Mounty were surface sterilized with 10% bleach solution for 10 minutes followed by 3 rinses with sterilized distilled water. Seeds were then dried in a laminar air flow hood for 3 hours. Seeds were then placed in petri-dishes on solidified agar medium containing various concentrations of different sources of the LCO illustrated in FIG. 1b (manufactured by Darmstadt, Germany and Grenoble, France) (also referred to in the examples as the "soybean LCO") and the inventive CO illustrated in FIG. 2a (also referred to in the examples as the "pea CO" or "CO-V"). Seedling roots were measured by a hand ruler and root fresh weights were taken in a micro balance at day 7. Growth study was done in a growth chamber at 22° C.

Figure 5:
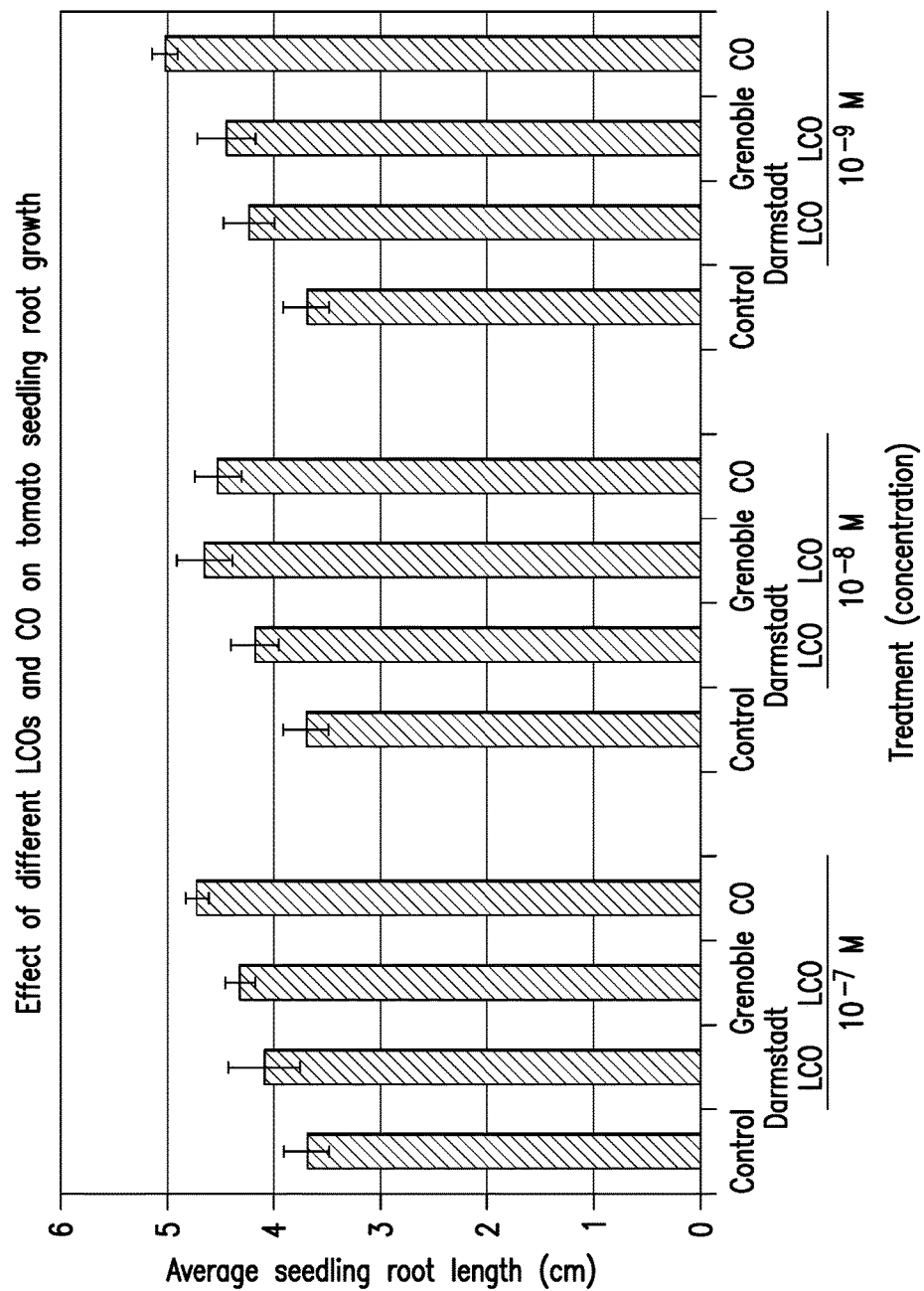
FIG. 5 is a bar graph that illustrates effect of an inventive CO (illustrated in FIG. 2a) at three different concentrations ($10^{-7}$, $10^{-8}$ and $10^{-9}$ M) compared to two different sources of the LCO illustrated in FIG. 1b, and a control, treated on tomato seeds, expressed in terms of seedling average root length.
Figure 6:
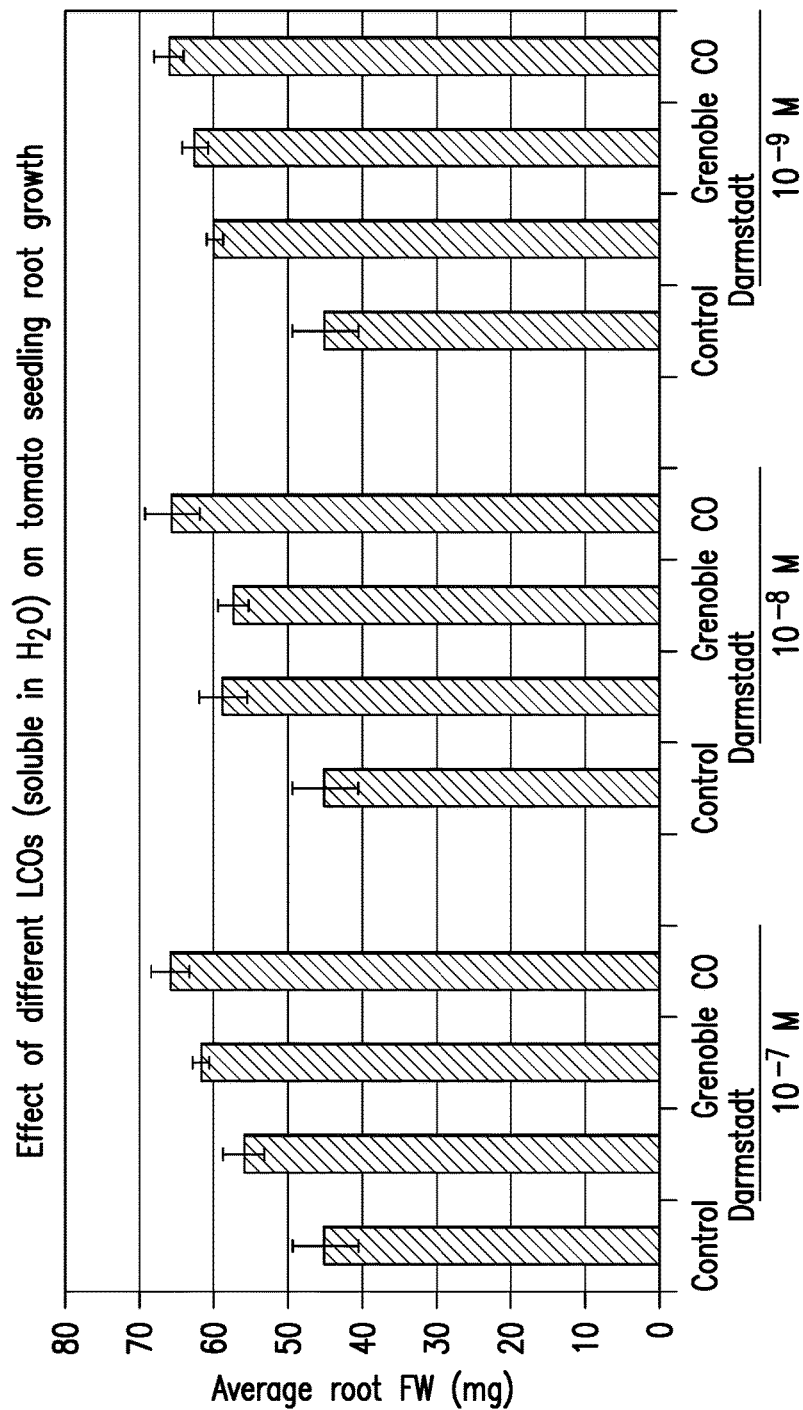
FIG. 6 is a bar graph that illustrates effect of the inventive CO (illustrated in FIG. 2a) at three different concentrations ($10^{-7}$, $10^{-8}$ and $10^{-9}$ M) compared to two different sources of the LCO illustrated in FIG. 1b, and a control, treated on tomato seeds, expressed in terms of seedling average root fresh weight.
Figure 7:
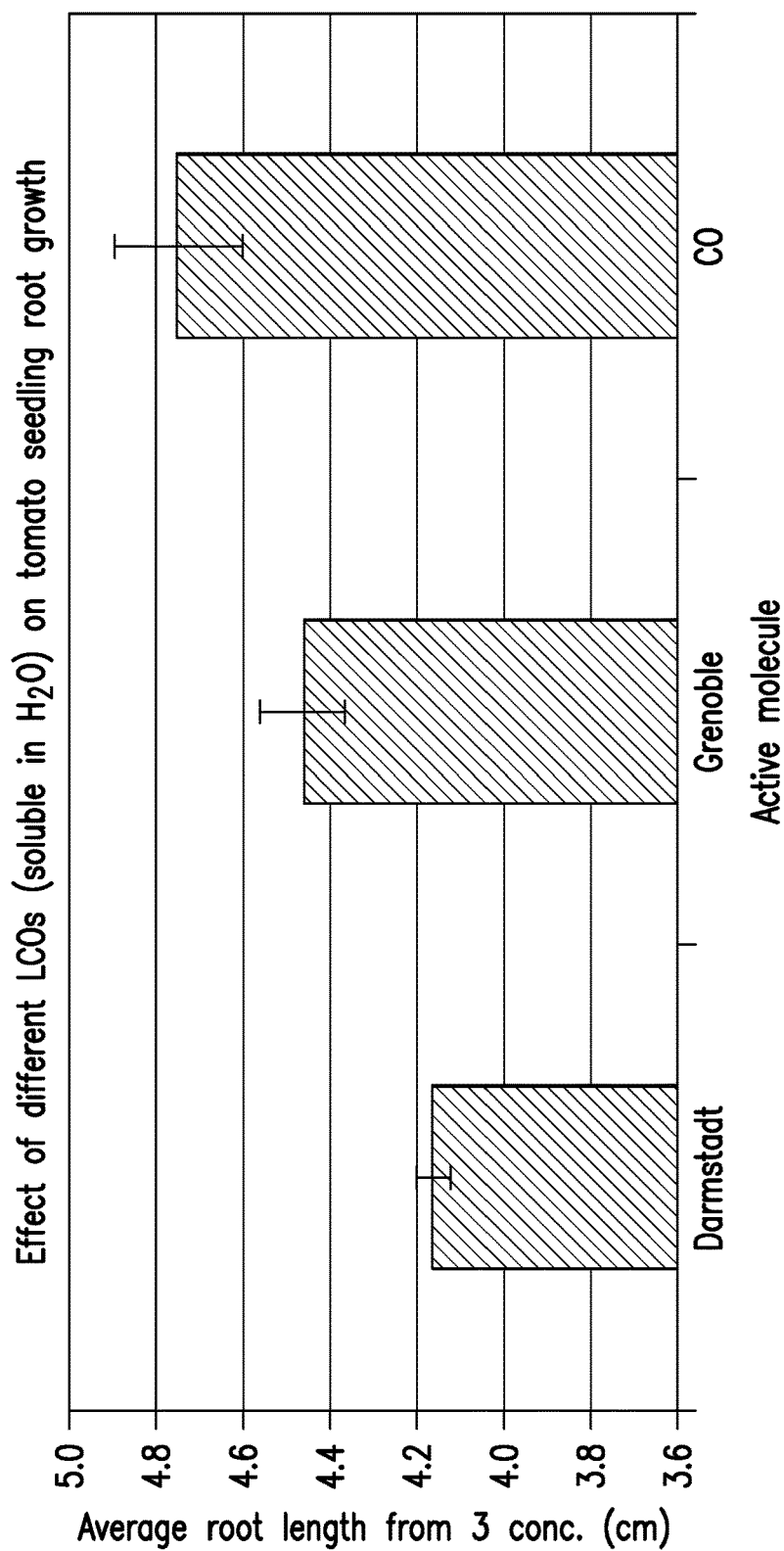
FIG. 7 is a bar graph that illustrates effect of the inventive CO (illustrated in FIG. 2a) at a mean concentration (of three concentrations) compared to two different sources of the LCO illustrated in FIG. 1b, treated on tomato seeds, expressed in terms of seedling average root length.
Figure 8:
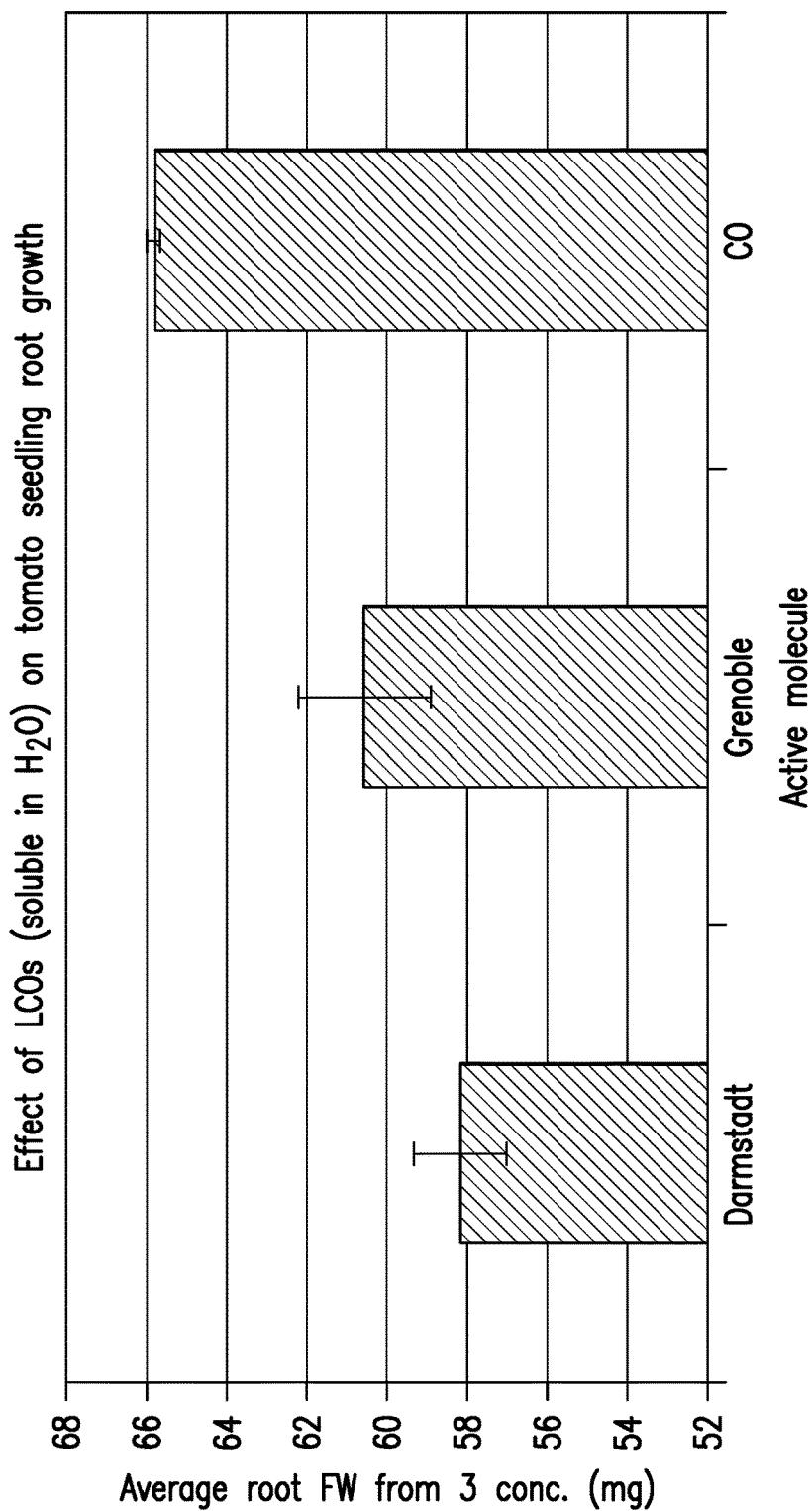
FIG. 8 is a bar graph that illustrates effect of the inventive CO (illustrated in FIG. 2a) at a mean concentration (of three concentrations) compared to two different sources of the LCO illustrated in FIG. 1b, treated on tomato plants, expressed in terms of seedling average root fresh weight.

As reflected by the comparison between Pea CO (inventive embodiment) and LCOs (non-inventive and comparable), the pea CO exhibited better (at $10^{-7}M$ and $10^{-9}M$) or equal (at $10^{-8}M$) to LCO when tomato seedling root length was measured (FIG. 5). In terms of seedling root fresh weight, Pea CO outperformed LCO at all three levels of concentrations (FIG. 6). Both LCOs and CO were significantly better than control seedlings in increasing root length and fresh weight. When the average root growth from all 3 concentrations was plotted, it appeared to be that CO is significantly better than LCOs in increasing tomato root growth (FIGS. 7 and 8).

Example 2: Cotton Foliar Experiment

Cotton seeds were planted and grown to V4 stage (4 leaved stages) and then were sprayed with $10^{-8}M$ of the LCO illustrated in FIG. 2b (also referred to in the examples as the "Pea LCO") and the pea CO and then left to grow up to 4 weeks with occasional watering with Hoagland solution. Control plants were sprayed with water.

Figure 9:
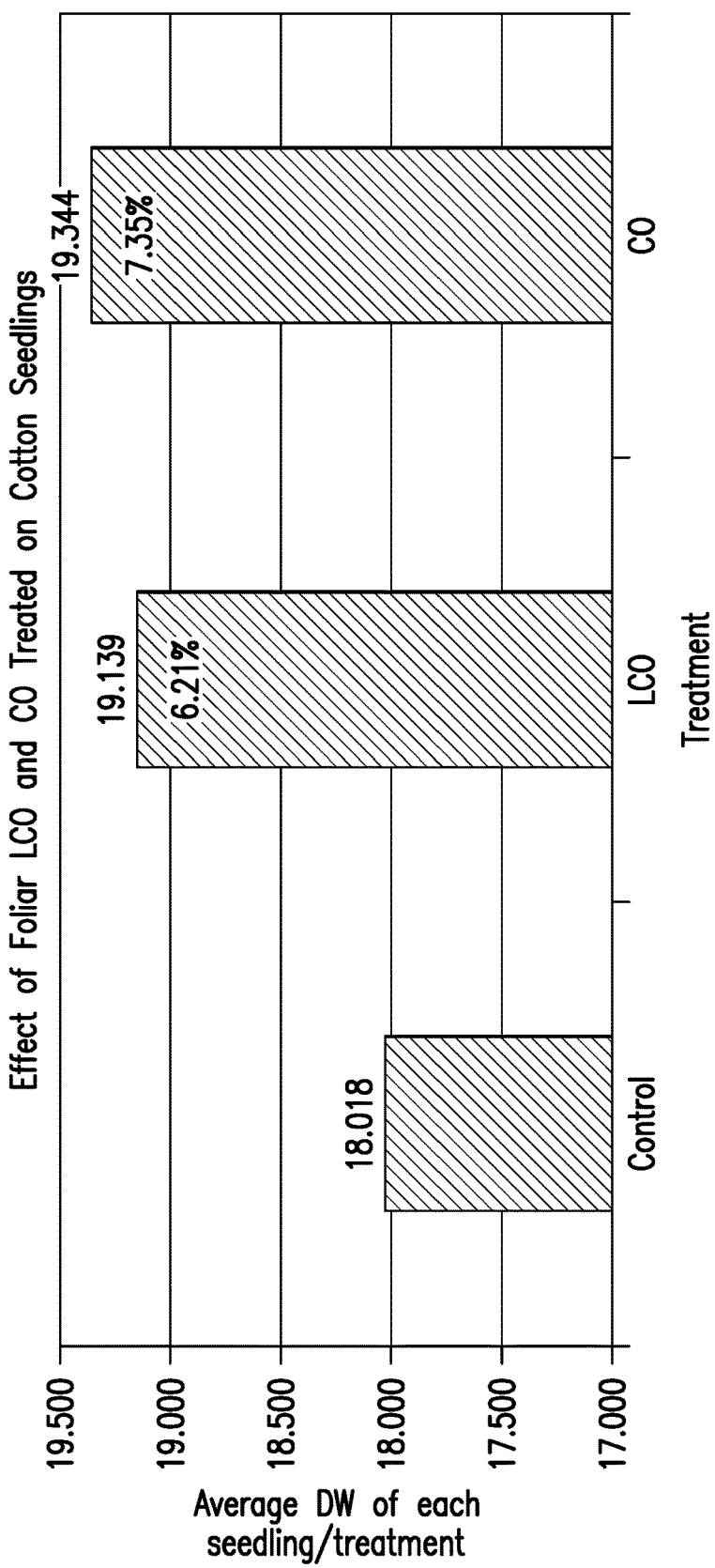
FIG. 9 is a bar graph that illustrates the effect of the inventive CO (illustrated in FIG. 2a) compared to the LCO illustrated in FIG. 2b, and a control, treated on cotton plants, expressed in terms of average dry weight of each seedling per treatment.

The results achieved by the inventive embodiment (CO) showed that both CO and LCO (non-inventive and comparable) significantly increased plant fresh weights over control but CO showed 1.14% more plant fresh weight increase over LCO (FIG. 9).

Example 3: Corn Seed Treatment

Two seed treatment experiments using only Pea LCO, Pea CO and the CO mixtures obtained from chitosan by enzymatic process (structurally distinct from the Pea CO, and also referred to in the examples as the "China CO") were performed in greenhouse. Hybrid corn seeds (92L90, Peterson Farm, USA) were treated with treatment solution ($10^{-8}$ M) at the rate of 3 fl oz/100 lbs of seed. Seeds were planted in plastic pots containing 1:1 Sand:Perlite mixture. Seeds were allowed to grow for about 3-4 weeks and then they were harvested and their dry weight measured.

Figure 10:
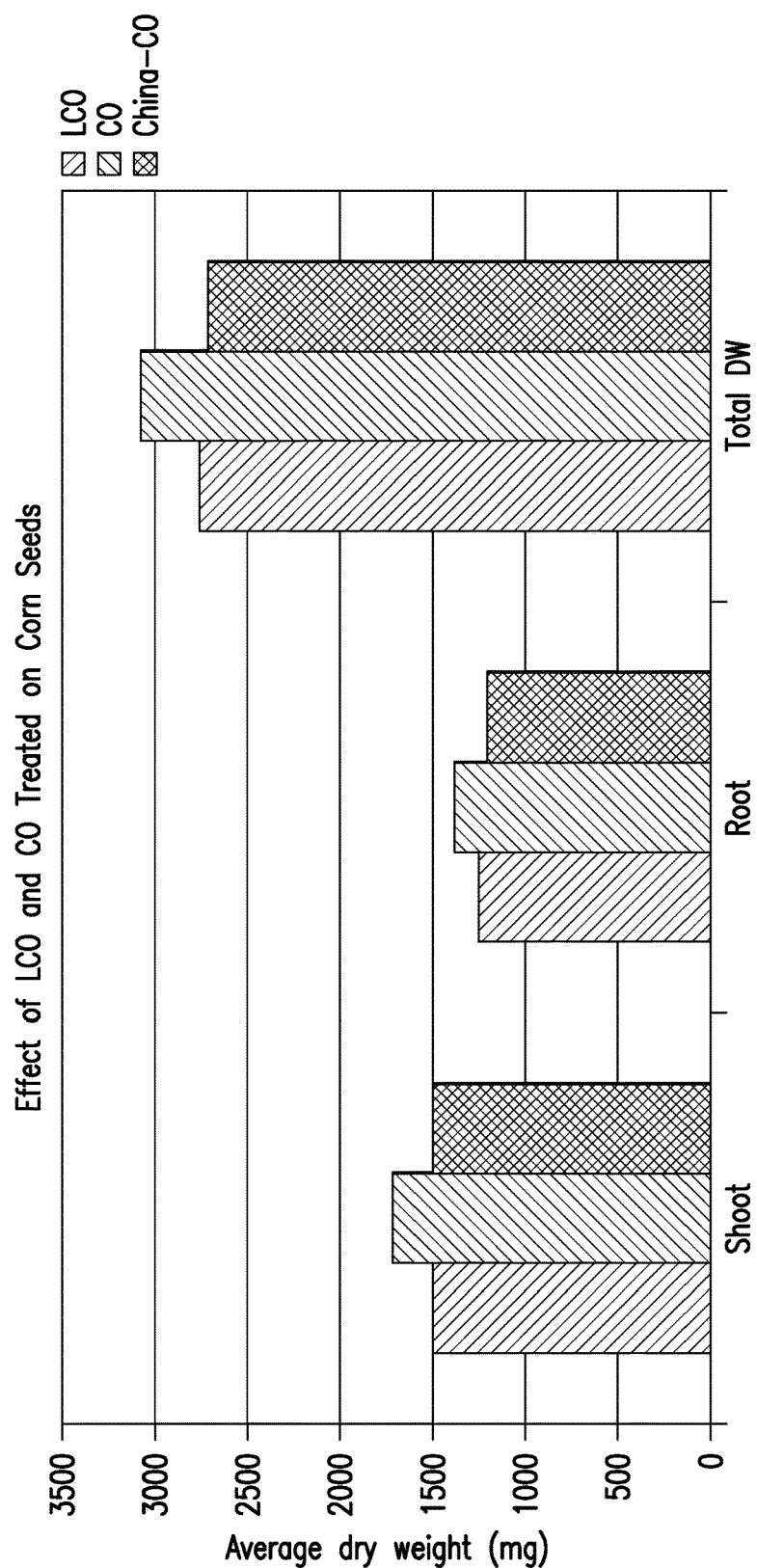
FIGS. 10 (trial 1) and 11 (trial 2) are bar graphs that show the effect of the CO illustrated in FIG. 2a, compared to the LCO illustrated in FIG. 2b, and a mixture of (non-inventive) chitinous compounds produced by chitinase, treated on corn seed, expressed in terms of average dry weight of shoots, roots and total dry weight (combined dry weight of shoots and roots).
Figure 11:
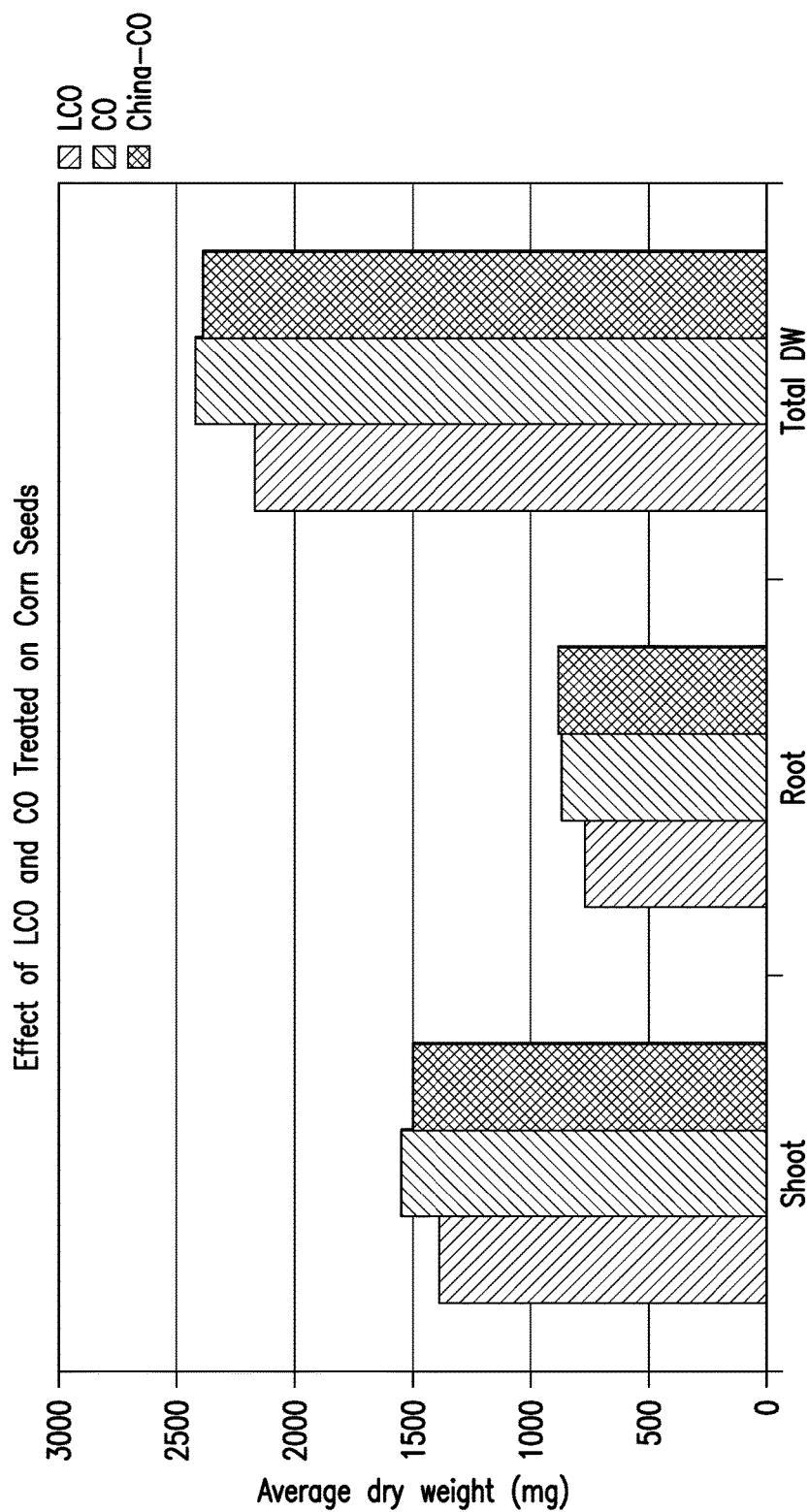

Results obtained from both experiments indicated that inventive (pea CO) showed greater shoot, root and total biomass increase over non-inventive and comparable LCO. For the first trial CO had 11.84% dry weight increase over LCO (FIG. 10). In the second trial, CO had 12.63% dry weight-increase over LCO (FIG. 11). China CO, which may also be considered as a substitute source of pea CO, also demonstrated increased plant dry weight increase as compared to non-inventive LCO.

Example 4: Treatment of Soybean with Various Actives

Soybean seeds (Jung seed, var. 8168NRR) were treated with various active molecules. Seeds were treated with a liquid dose rate of 3 fl oz/100 lbs of seed. Seeds were allowed to dry for a 2 hours and planted in greenhouse in plastic pots containing 1:1 sand:perlite mixture. Seedlings were grown for 4 wks with occasional liquid fertilizer applications and then the plants were harvested. The central leaflet from the $2^{nd}$ trifoliate (from down to top) was isolated and measured for surface area on a WinRhizo scanner. The rest of the plants were used for plant dry weight (DW).

Figure 12:
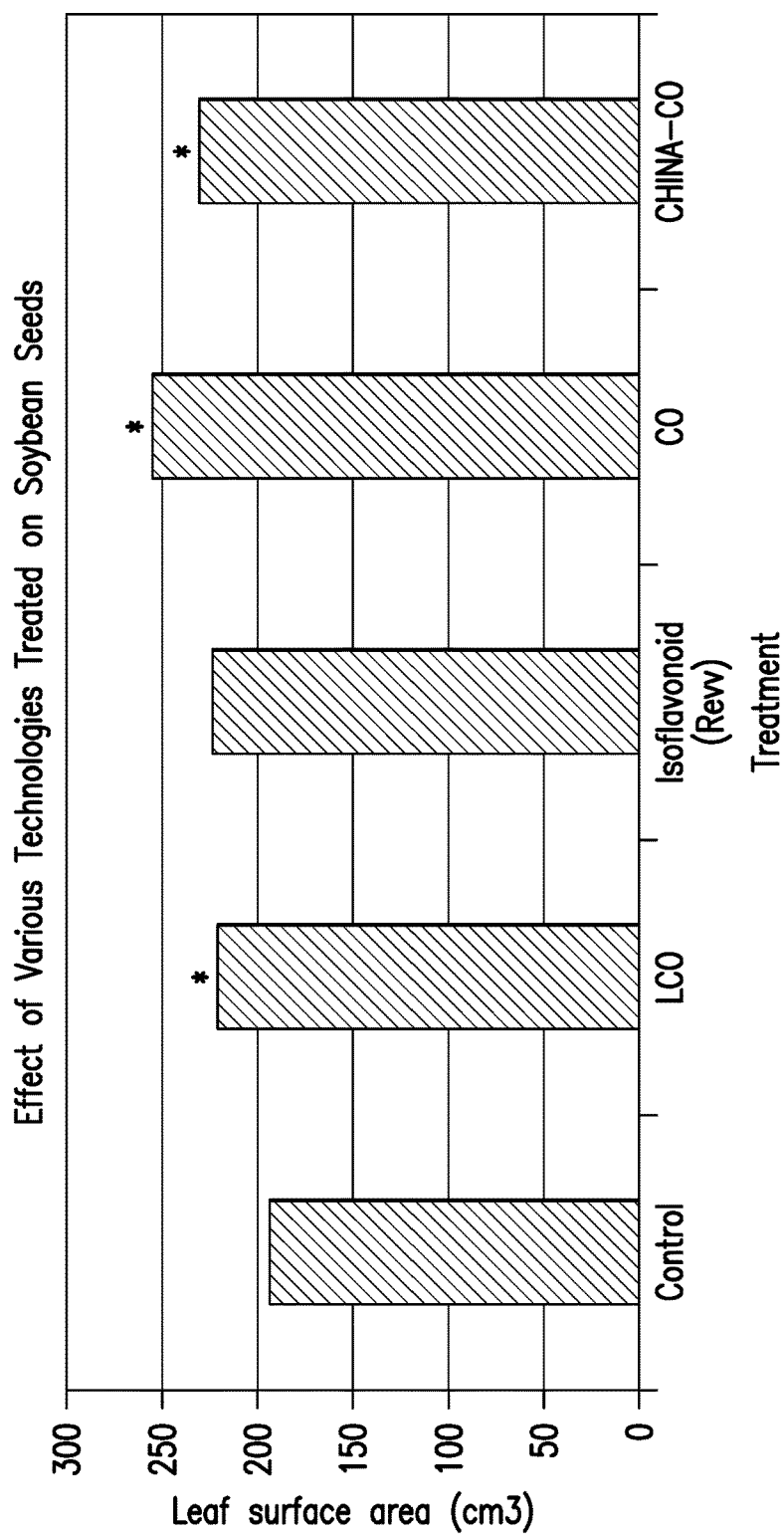
FIG. 12 is a bar graph that illustrates the effect of the CO illustrated in FIG. 2a, compared to the LCO illustrated in FIG. 2b, a mixture of CO's produced by chitinase, an isoflavonoid, and a control, treated on soybean seed, expressed in terms of leaf surface area.
Figure 13:
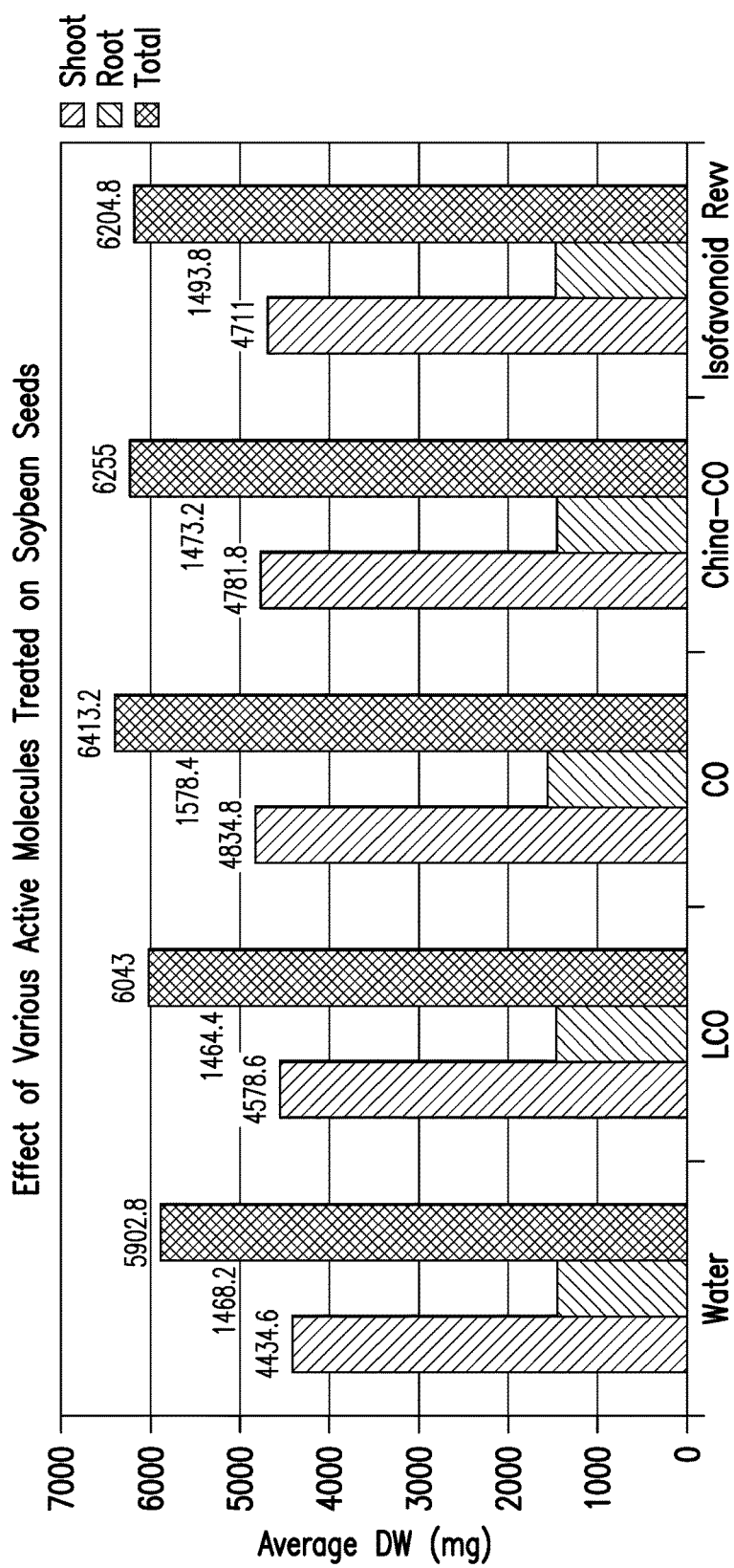
FIG. 13 is a bar graph that illustrates the effect of the CO illustrated in FIG. 2a, the LCO illustrated in FIG. 1b, an isoflavonoid, and the mixture of the non-inventive chitinous compounds (obtained from chitosan via an enzymatic process), treated on soybean seeds, expressed in terms of average dry weight of soybean plant.

Results obtained from the experiment elucidated that non-inventive pea LCO, the inventive pea CO and the China CO showed significant increase in leaf surface area. But among these three actives, the pea CO produced the highest leaf surface area (significantly higher than the control (water)) and relatively higher than Chinese CO (FIG. 12). In another experiment, CO produced the highest plant dry weights in terms of either shoot, or root or total plant biomass. Thus, it was evident that the biomass increase by CO was better than the soybean LCO or any other treatments including water as a control and isoflavonoids as a separate plant signal molecule (FIG. 13).

Example 5: Root Hair Deformation Bioassay

Siratro (*Macroptelium atropurpureum*) seeds were germinated on moist filter paper in petriplates. When seedlings roots are about 1-inches long, they are severed from the seedlings and treated with 2 ml of $10^{-8}M$ treatment solutions in test tubes for 4 hours in the dark. After treatment time is over the solutions are dyed with Congo Red for 10 minutes. After that root segments are observed under a compound microscope to count the number of deformed root hairs in the most sensitive zone of the root segment. Root hair deformation bioassay was also performed using Red Clover in a similar fashion like Siratro above and only visual observation was made and recorded in text form.

Figure 14:
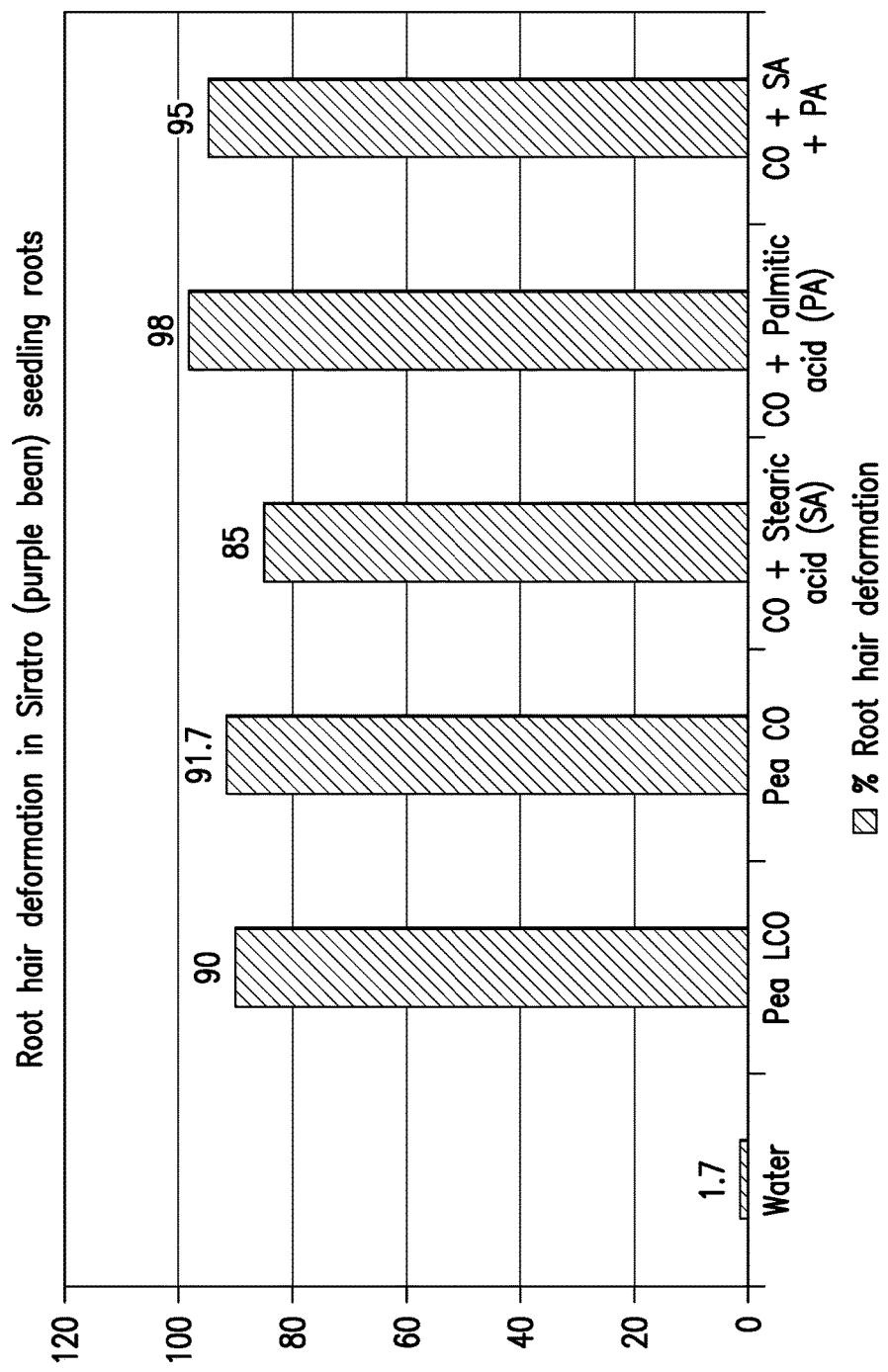
FIG. 14 is a bar graph that illustrates the effect of the CO illustrated in FIG. 2a, alone or in combination with one or two fatty acids, compared to the LCO illustrated in FIG. 2b, and water, on deformation of Siratro root hair, expressed in terms of percent.

Both LCO and CO solutions induced root hair deformation in the root segments (FIG. 14). CO and fatty acid (Stearic acid or Palmitic acid) combinations also showed root hair deformation with CO plus Palmitic acid and CO plus both Palmitic acid and Stearic acid providing numerically better root hair deformation than the LCO or CO. Overall, CO was equal to LCO in root hair deformation response. Palmitic acid addition improved deformation response. Control or CHK was treated with distilled water.

Root hair deformation pattern in Red Clover was much better and prominent for CO as compared to LCO. CO with either Palmitic acid or Stearic acid had similar deformation pattern like LCO. Overall, CO was the best root hair deformer in Red Clover.

Example 6: Canola and Wheat Seed Germination

Figure 15:
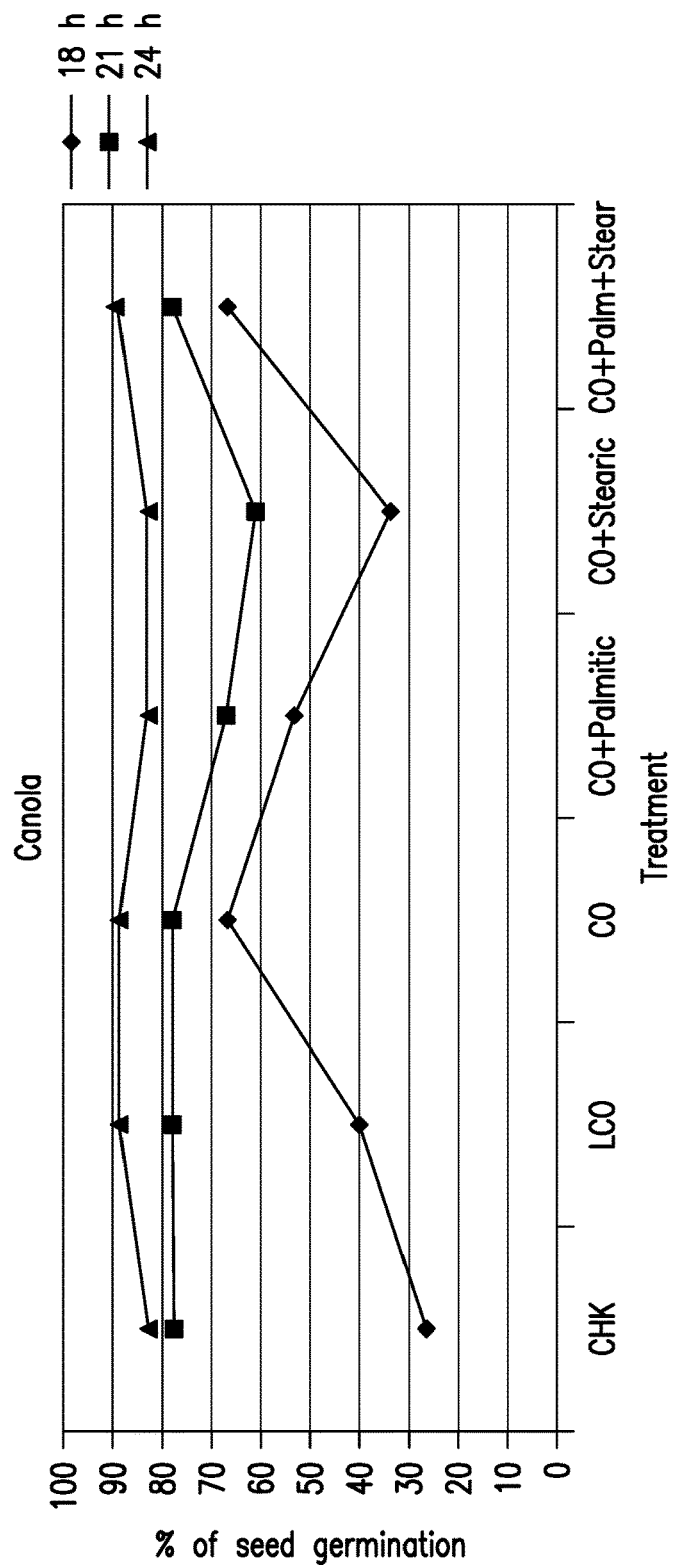
FIG. 15 is a graph that illustrates effect of the CO illustrated in FIG. 2a, alone or in combination with one or two fatty acids, compared to the LCO illustrated in FIG. 2b, and water, treated on canola seed, expressed in terms of percent of seed germination.
Figure 16:
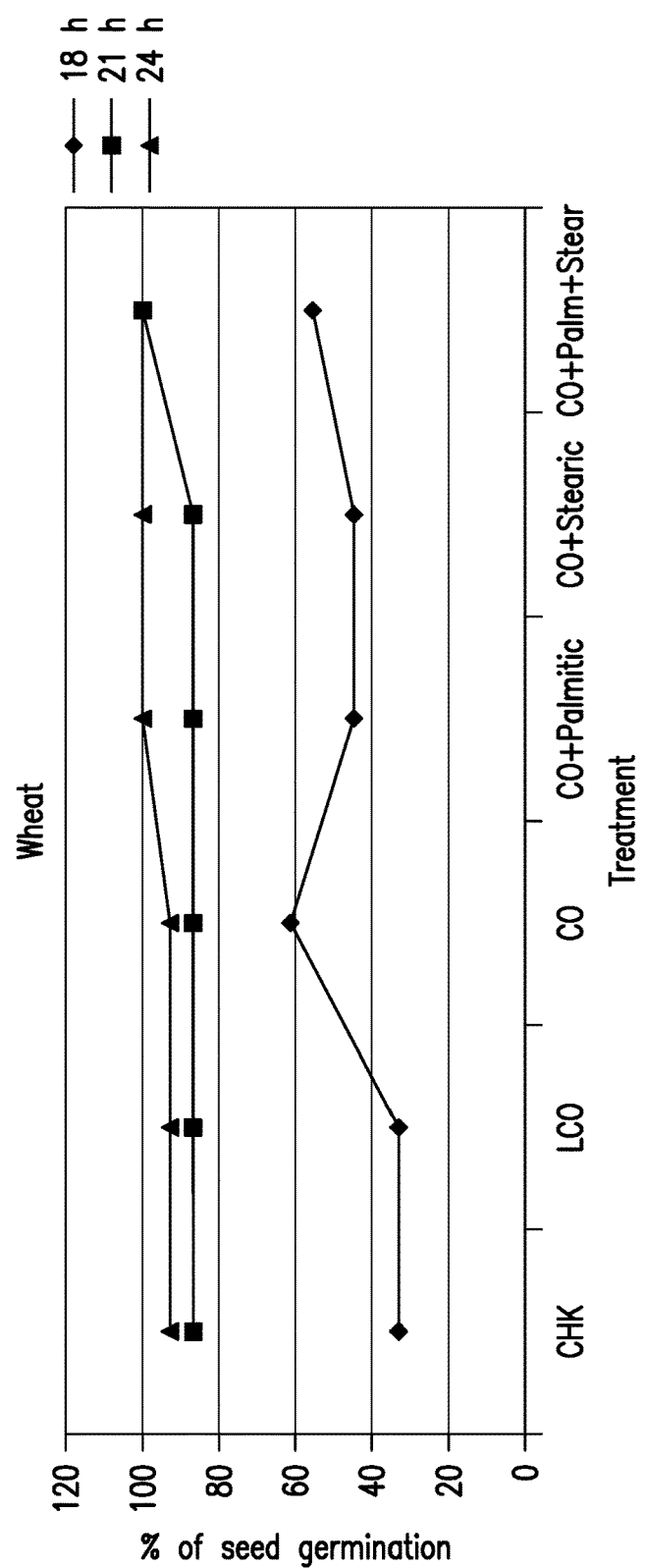
FIG. 16 is a graph that illustrates effect of the CO illustrated in FIG. 2a, alone or in combination with one or two fatty acids, compared to the LCO illustrated in FIG. 2b, and water, treated on wheat seed, expressed in terms of percent of seed germination.

In petriplates on moist filter paper moistened with $10^{-9}$ M treatment solution, canola and wheat seeds were plated for germination. At 18 h after plating, Pea CO induced more canola and wheat seed germination as compared to Pea LCO. Over the period of 21 to 24 hours, seed germination rate for LCO and CO leveled up. The experiment shows an early germination induction by CO over LCO (FIGS. 15 and 16).

Example 7: Alfalfa Seed Germination

Figure 17:
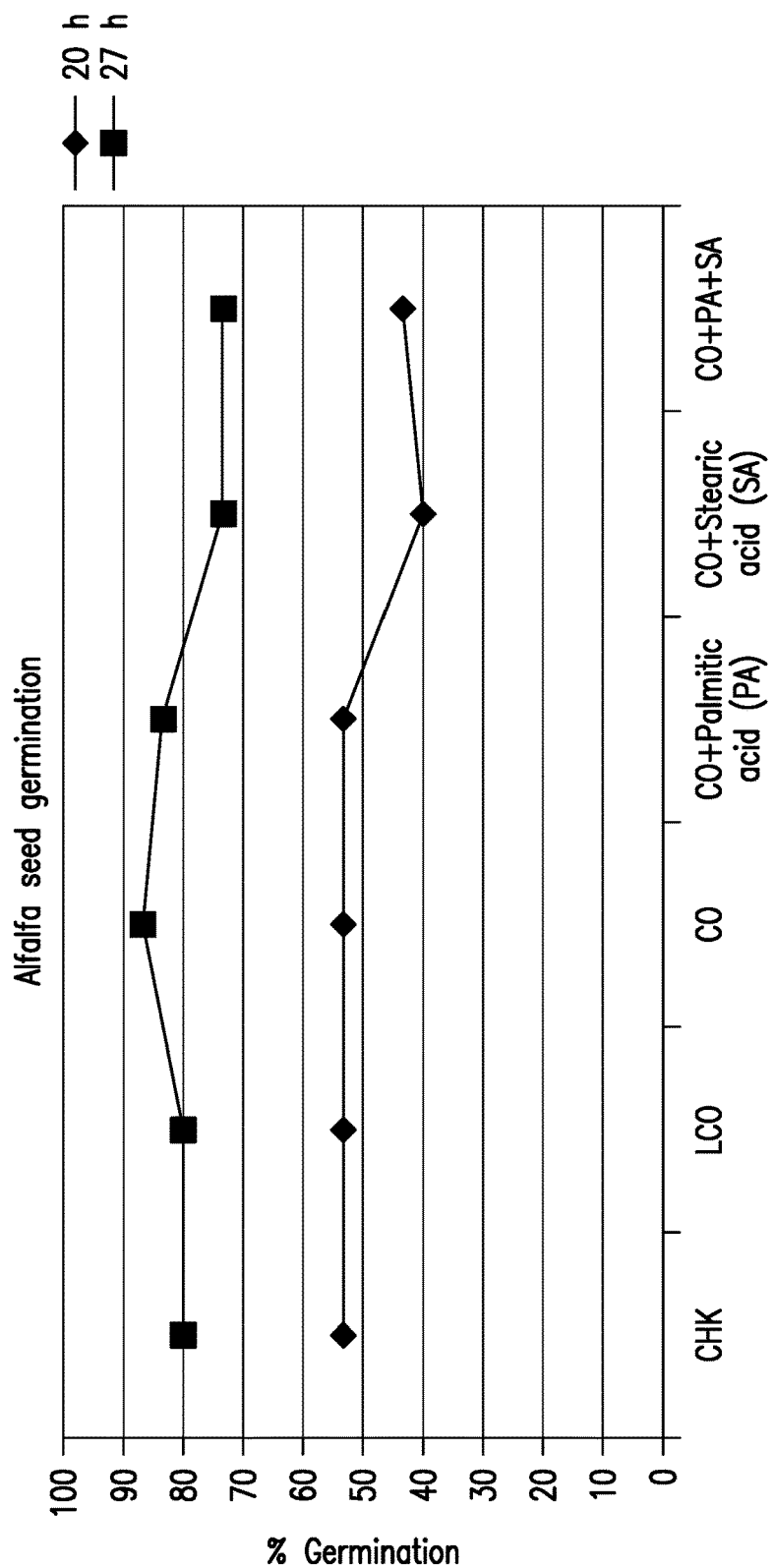
FIG. 17 is a graph that illustrates effect of the CO illustrated in FIG. 2a, alone or in combination with one or two fatty acids, compared to the LCO illustrated in FIG. 2b, and water, treated on alfalfa seed, expressed in terms of percent of seed germination.

Alfalfa (*Medicago sativa*) seeds were germinated in petriplates on moist filter paper containing Pea LCO and Pea CO treatment solutions ($10^{-8}$ M) and petriplates were kept in the dark at room temperature (22° C.). After 20 and 27 h, the seeds were observed for germination. At 20 h, there was no difference in germination rate among control, LCO and CO but at 27 h, CO showed 6% more germination over control and LCO. It showed that Pea LCO may not be effective on alfalfa seeds but pea CO could positively impact seed germination over control and pea LCO (FIG. 17).

Example 8: Corn and Wheat Seed Germination in Petriplates

Corn and wheat seeds were plated in petriplates containing 5 ml of treatment solution on a filter paper. Corn seeds were placed on moist filter paper for germination. Similarly, wheat seeds (spring wheat) were placed in petriplates. Corn and wheat seeds were observed for germinated seedlings 5 days after plating. Roots were harvested and their length measured by WinRhizo system.

Figure 18:
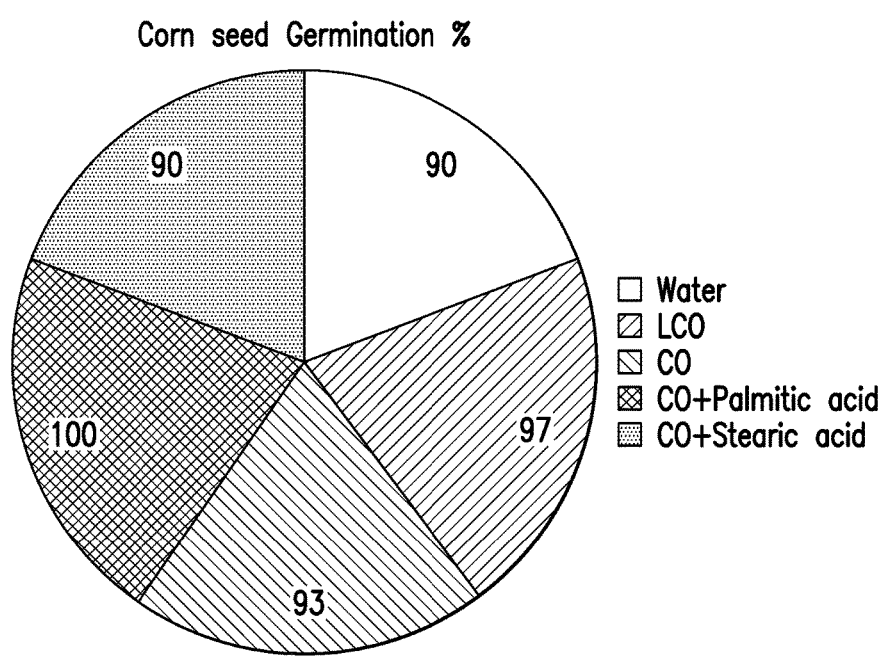
FIG. 18 is a pie-chart that illustrates the effect of the CO illustrated in FIG. 2a, alone or in combination with one of two different fatty acids, compared to the LCO illustrated in FIG. 2b, and water, treated on corn seed, expressed in terms of percent of seed germination.
Figure 19:
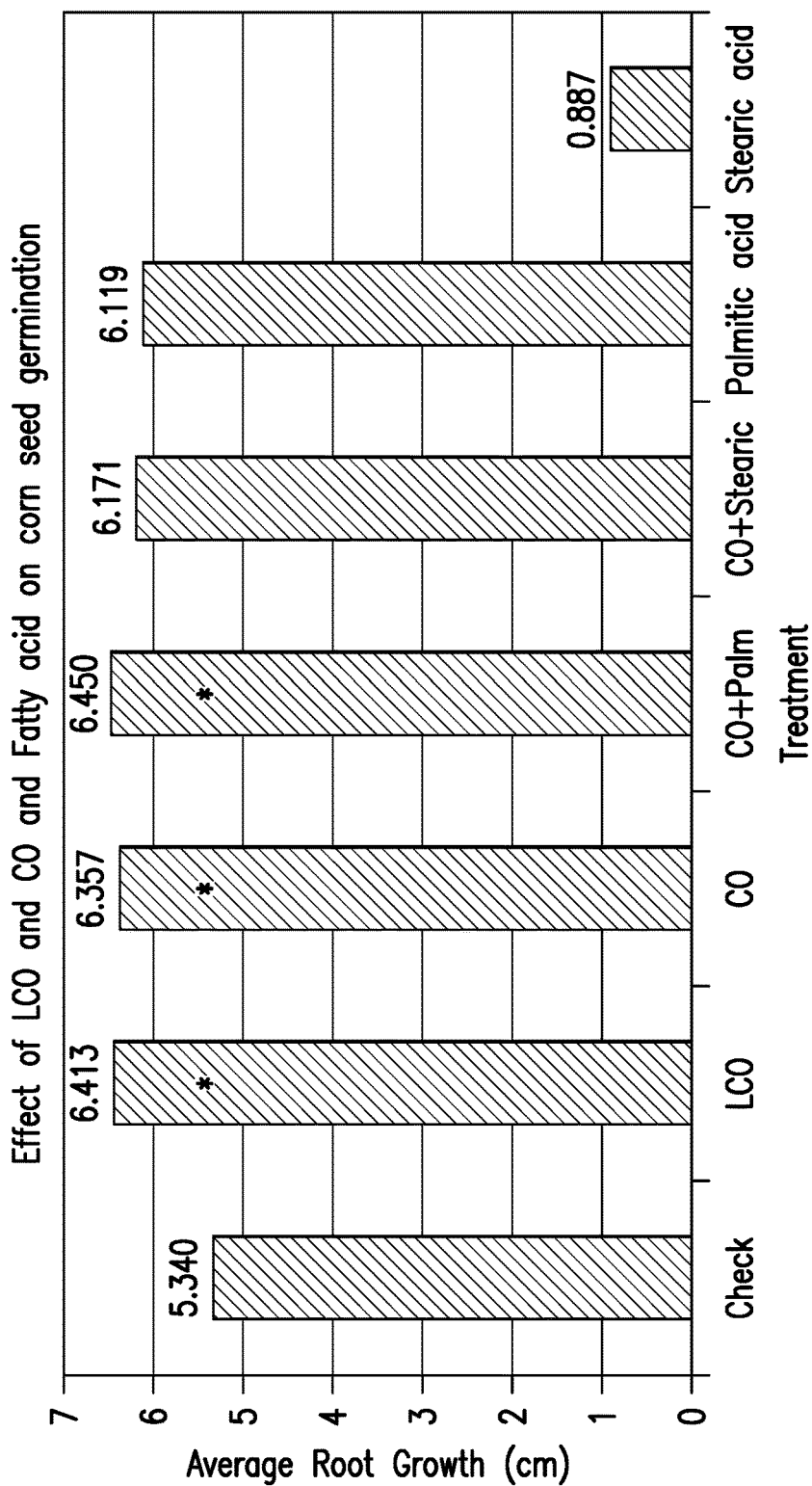
FIG. 19 is a graph that illustrates effect of the CO illustrated in FIG. 2a, alone or in combination with one of two different fatty acids, compared to the LCO illustrated in FIG. 2b, each of the fatty acids alone, and a control, treated on corn seed, expressed in terms of percent of seed germination.
Figure 20:
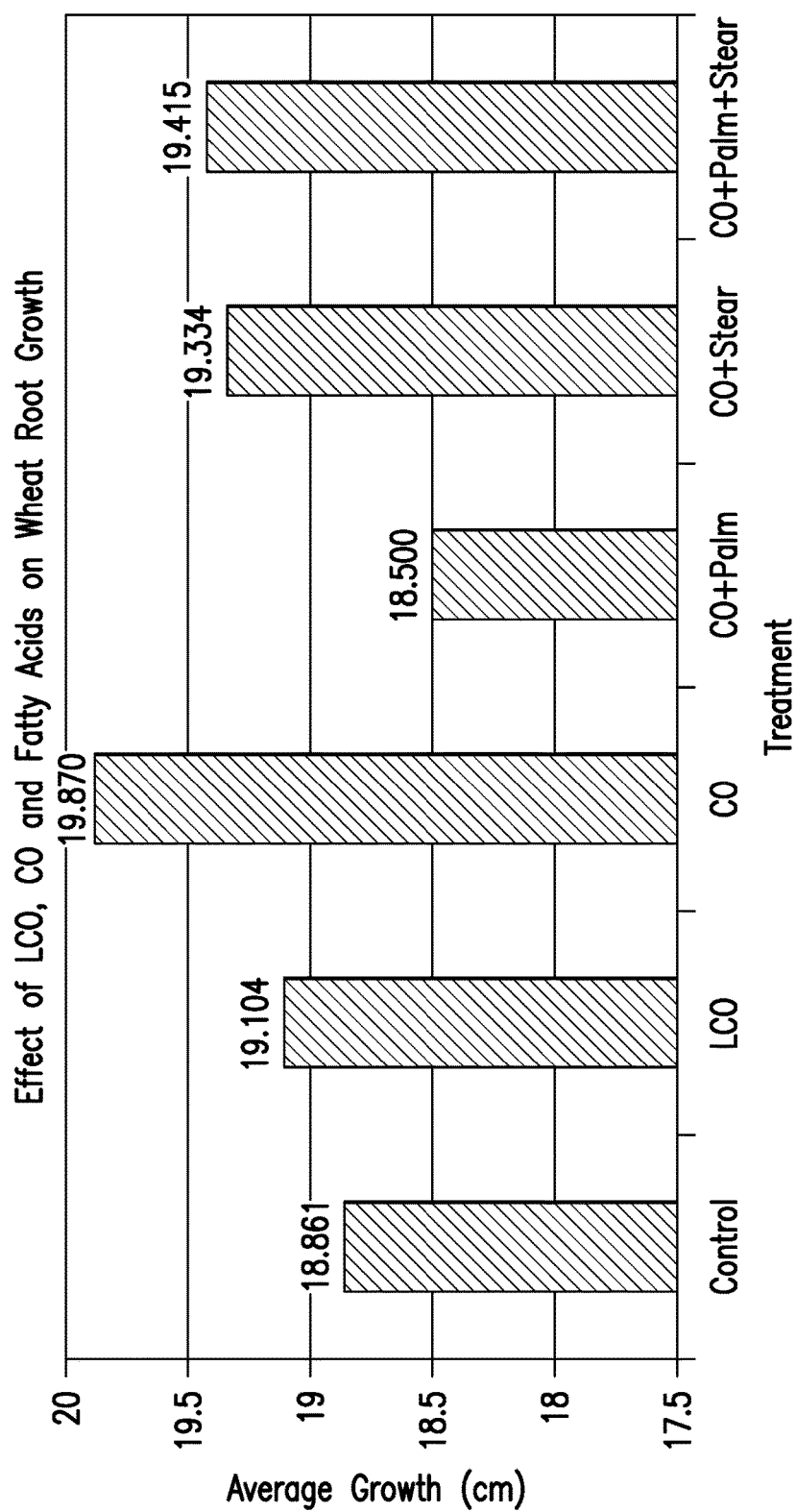
FIG. 20 is a graph that illustrates effect of the CO illustrated in FIG. 2a, alone or in combination with one of two different fatty acids, the CO plus both fatty acids, compared to the LCO illustrated in FIG. 2b, and a control, treated on wheat seed, expressed in terms of percent of seed germination.

In corn, Pea LCO, Pea CO and CO with Palmitic acid showed increased germination (FIG. 18) and they significantly increased seedling root length over control as well. Their effect was not statistically different, CO with Palmitic acid being the highest for germination and root length. Addition of Palmitic acid with CO seemed to be slightly beneficial (not statistically) over LCO or CO (FIG. 19). In wheat, CO outperformed LCO by producing longer roots. The increase in root length by LCO and CO in wheat was not statistically significant but consistently greater (FIG. 20).

Example 9: Common Vetch (*Vicia sativa*) Seed Germination

Common vetch seeds were plated in petriplates containing 5 ml of treatment solutions on filter paper. Seed germination at 22° C. was counted after 24 h and seedling root length was measured at day 5 with WinRhizo system.

Figure 21:
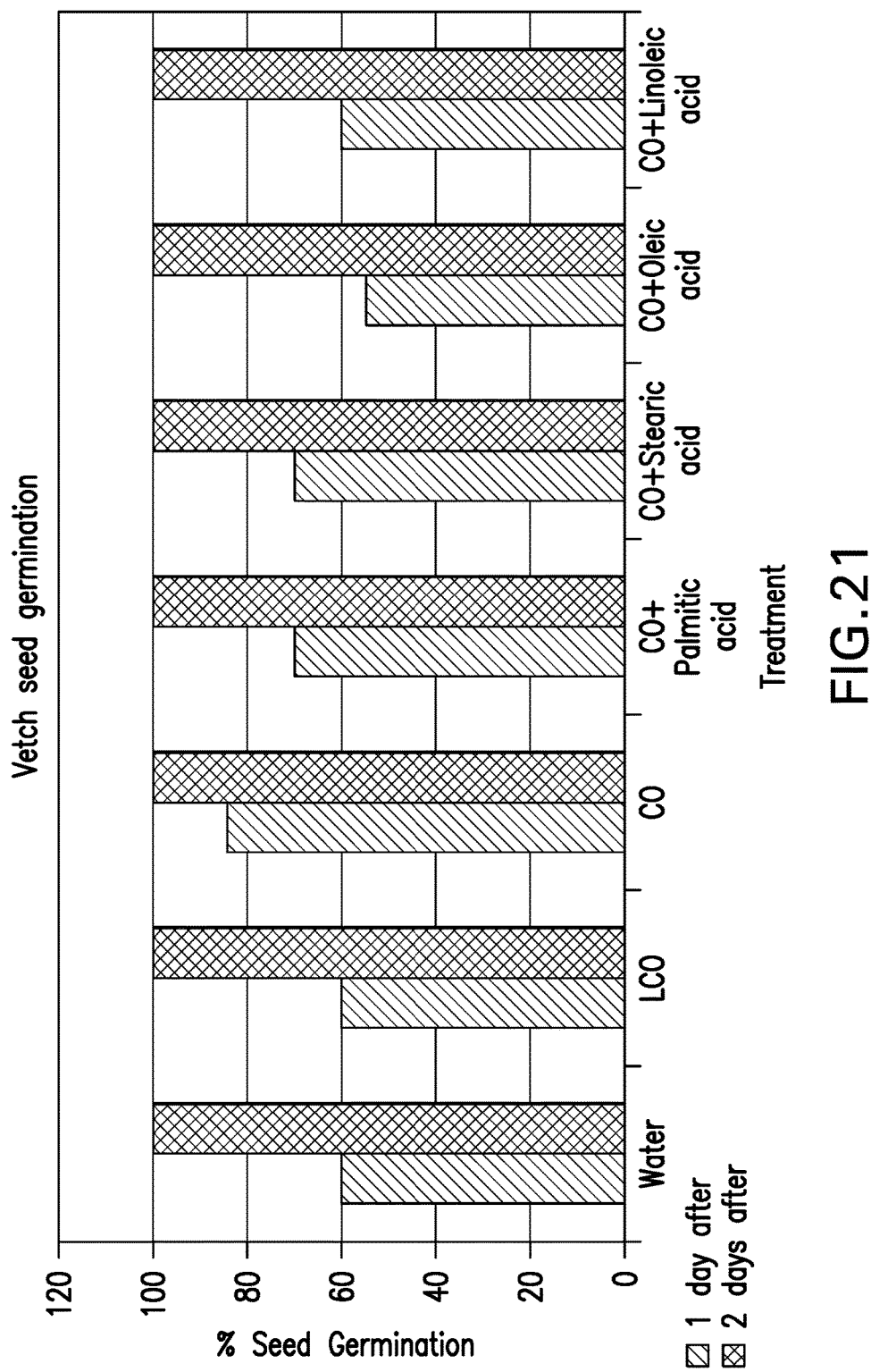
FIG. 21 is a bar graph that illustrates effect of the CO illustrated in FIG. 2a, alone or in combination with one of four different fatty acids, compared to the LCO illustrated in FIG. 2b, and water, treated on *Vicia sativa* seed, expressed in terms of percent of seed germination.
Figure 22:
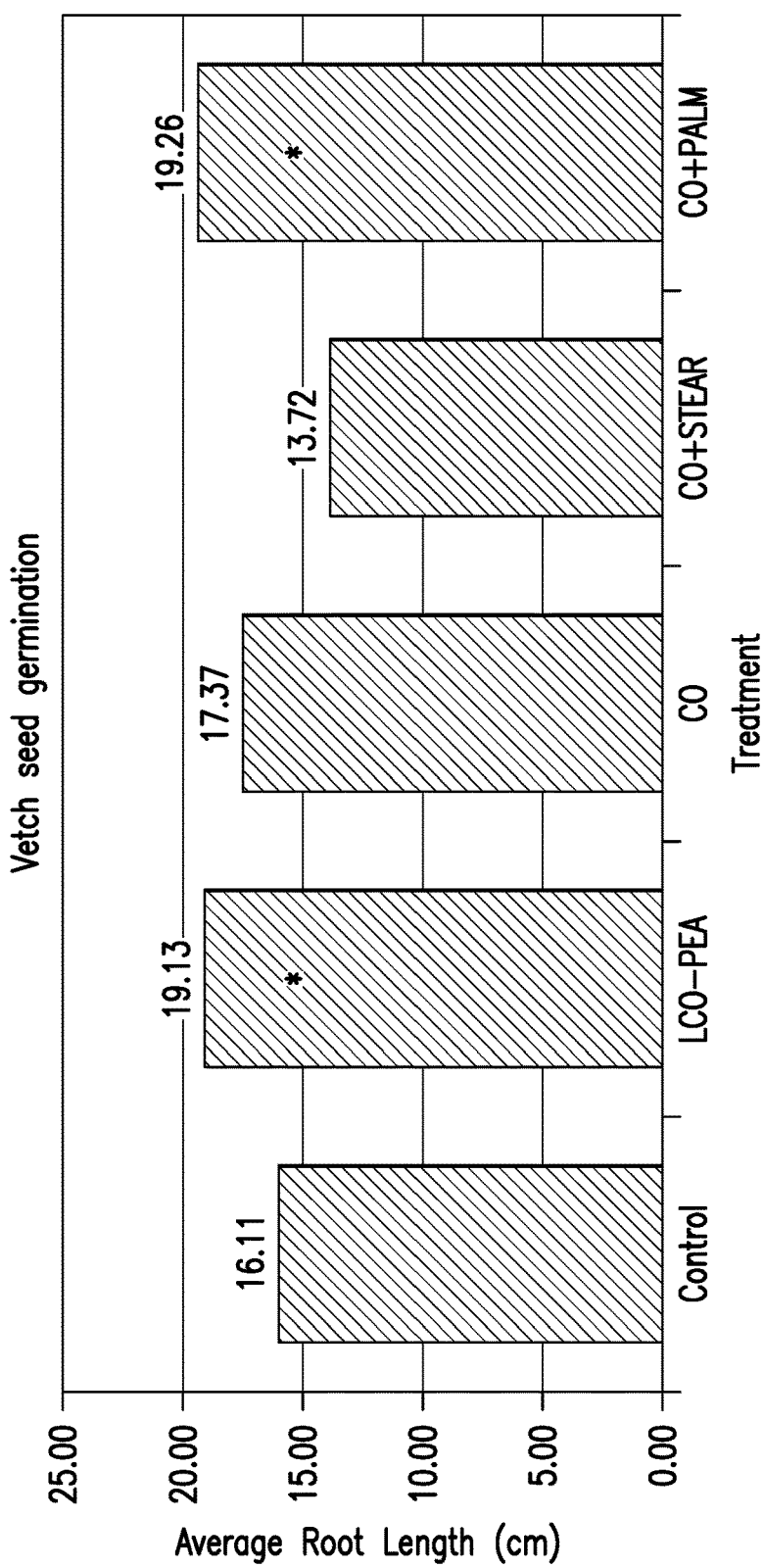
FIG. 22 is a bar graph that illustrates effect of the CO illustrated in FIG. 2a, alone or in combination with one of two different fatty acids, compared to the LCO illustrated in FIG. 2b, and a control, treated on the roots of *Vicia sativa*, expressed in terms of average root length.

In germination experiment Pea LCO, and Pea CO in combination with 4 different fatty acids were used. It was found that CO alone or with either Palmitic acid or Stearic acid induced early seed germination. One day after plating in petriplates, CO had 25% more germination over control and LCO (FIG. 21). When root length was measured, only LCO and CO with Palmitic acid significantly increased seedling root length over control (FIG. 22).

Example 10: Seed Germination in Multiple Crops

Similar to the seed germination experiment mentioned above, seeds of different crops were placed on moist filter paper in petriplates containing 5 ml liquid in each. Petriplates with seeds were then kept in the dark at 22° C. After 24 h (except for Lab Lab which was 30 h), seeds were observed for germination.

Figure 23:
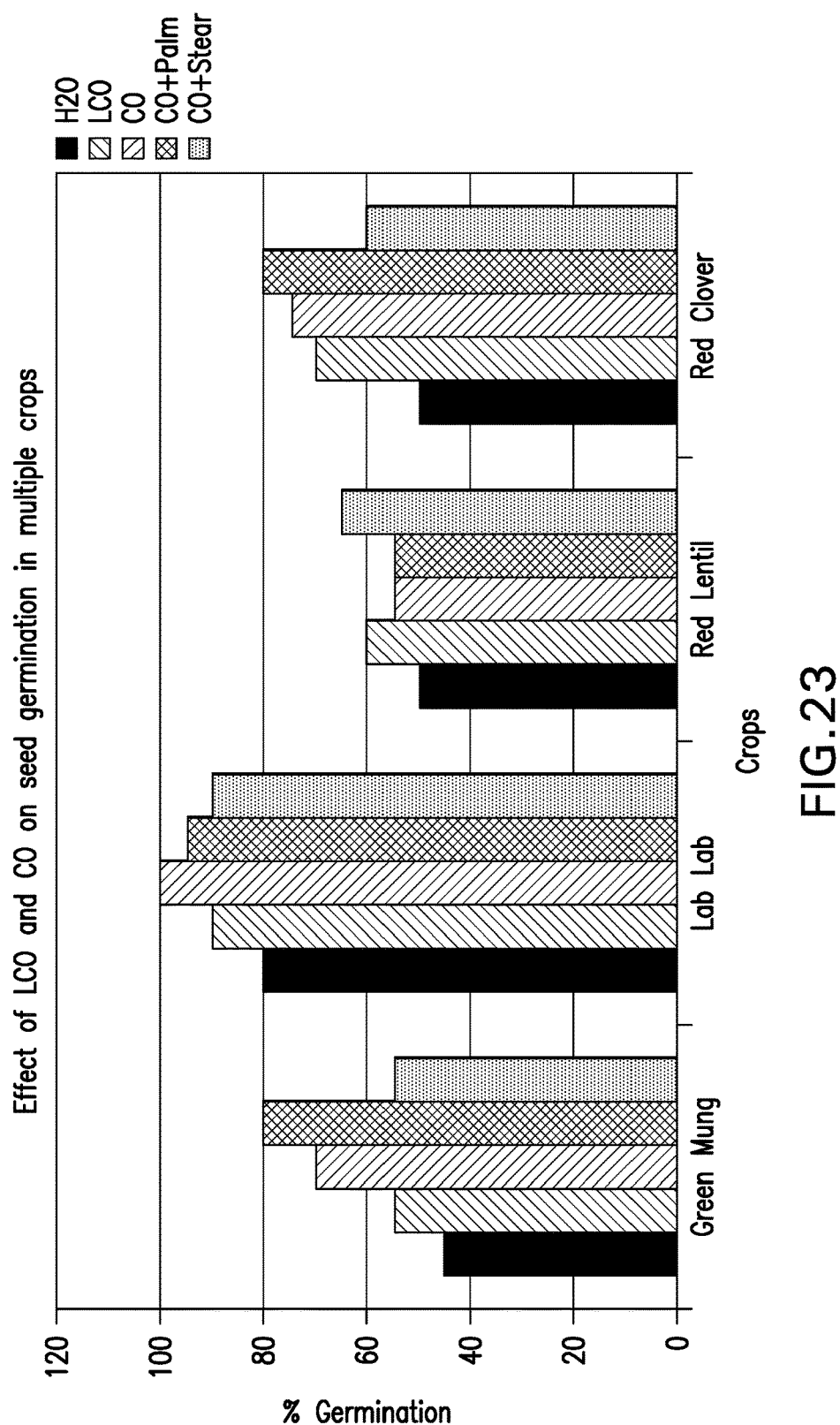
FIG. 23 is a bar graph that illustrates effect of the CO illustrated in FIG. 2a, alone or in combination with one of two different fatty acids, compared to the LCO illustrated in FIG. 2b, and water, treated on green mung, lab lab, red lentil and red clover seed, expressed in terms of percent of seed germination.

Overall seed germination by Pea CO was better than Pea LCO. Out of four crops (Green Mung, Lab Lab, Red Lentil and Red Clover), CO showed better germination in three crops except for Red Lentil (FIG. 23). CO plus Palmitic acid induced the highest germination in Green Mung and Red Clover. LCO was only better than CO or CO plus Palmitic acid for Red Lentil.

Example 11: Tomato Seedling Root Growth

In petriplate seed germination process, tomato Var. Royal Mounty seeds ware placed on moist filter paper soaked with 5 ml treatment solution. At 22° C. and after 5 days in dark, tomato seedling roots were measured for growth by WinRhizo system.

Figure 24:
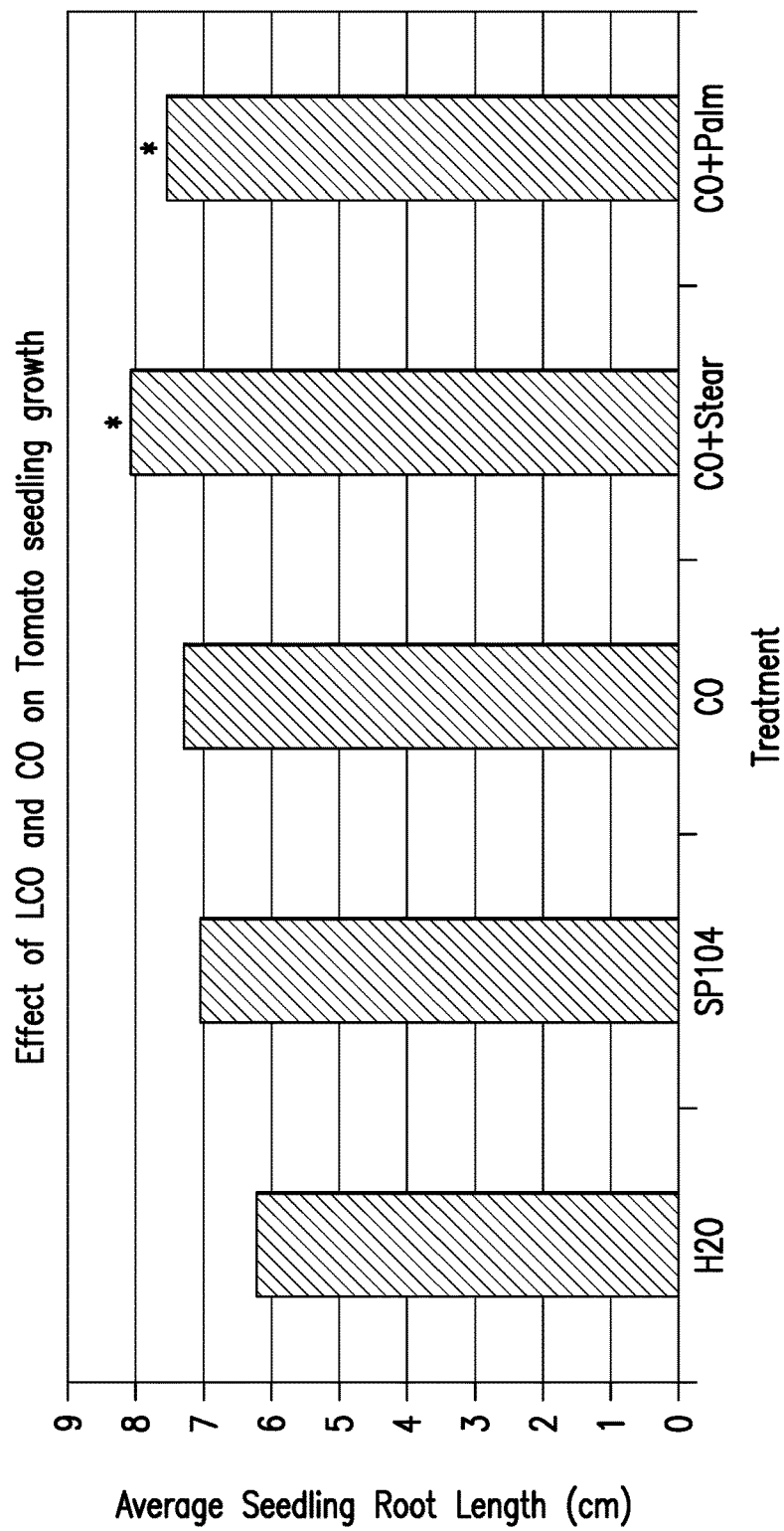
FIG. 24 is a bar graph that illustrates effect of the CO illustrated in FIG. 2a, alone or in combination with one of two different fatty acids, compared to the LCO illustrated in FIG. 2b, and water, on tomato seedling growth, expressed in terms of average root length.

Pea LCO, Pea CO and CO with fatty acids all showed increased root length as compared to water control. Average seedling root length by CO was better than LCO but it was not significantly better. CO with either Palmitic or Stearic acid significantly increased tomato seedling root length (FIG. 24).

Example 12: Soybean Seed Treatment

Soybean seeds (Pioneer 9oM80) were plated in petriplates on moist germination paper soaked with 5 ml of treatment solution containing either water or Soybean LCO, Pea CO and CO plus fatty acids. Seedling radicles were isolated after 48 hours and measured for their length.

Figure 25:
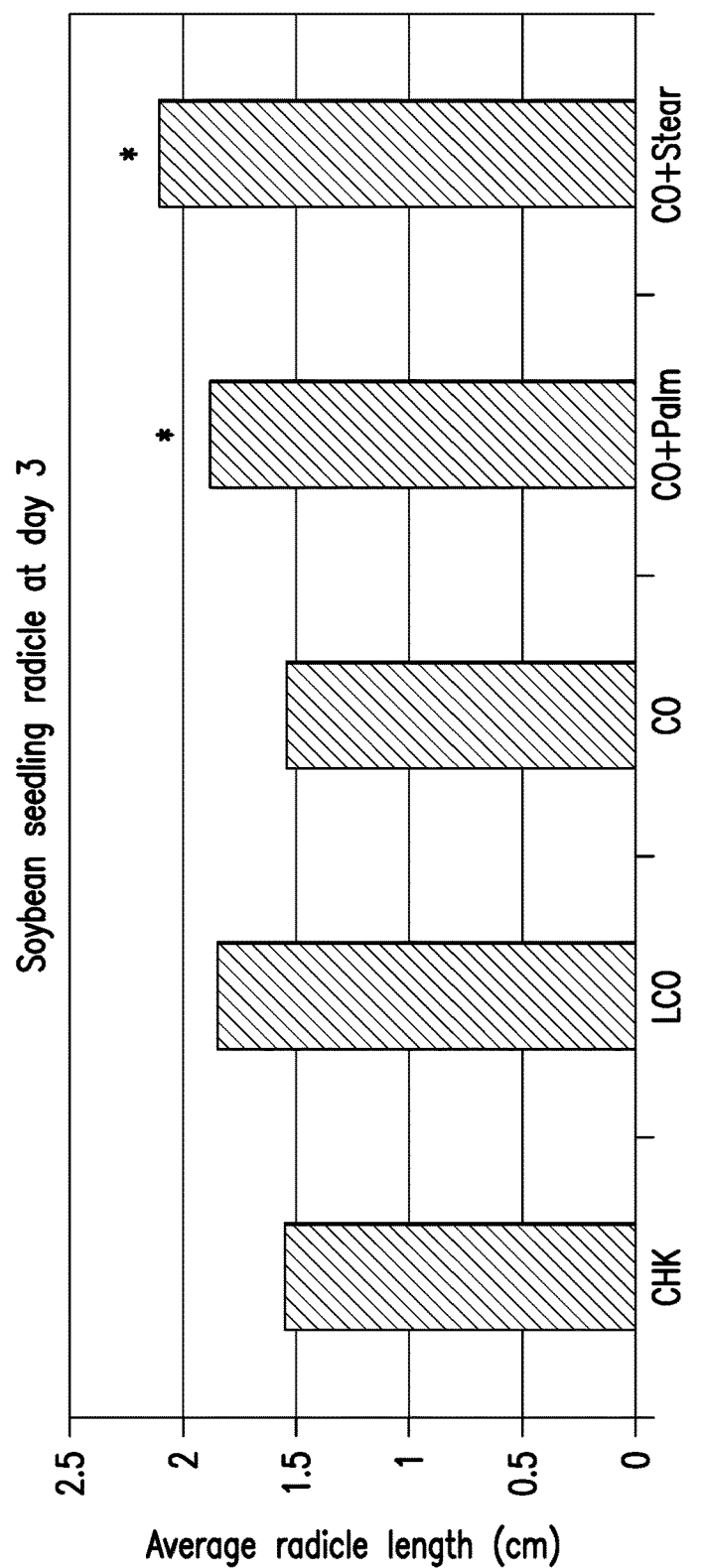
FIG. 25 is a bar graph that illustrates effect of the CO illustrated in FIG. 2a, alone or in combination with one of two different fatty acids, compared to the LCO illustrated in FIG. 1b, on soybean seed, expressed in terms of average radicle length.

LCO showed better seed radicle growth enhancement over control and CO but it was CO plus Stearic acid or Palmitic acid that exhibited significant increase in radicle length. CO itself is less effective that LCO on soybean but addition of fatty acid either Palmitic or Stearic acid with CO could further enhance seedling radical growth (FIG. 25).

Example 13: Cotton Seed Treatment

Cotton seeds were treated with LCO and CO $10^{-8}$M treatment solutions at a dose rate of 3 fl oz/100 lbs of seed. Seeds were planted the very next day in plastic pots containing 1:1 sand:perlite mixture. Seeds were grown in greenhouse for 4 wks and then they were harvested.

Figure 26:
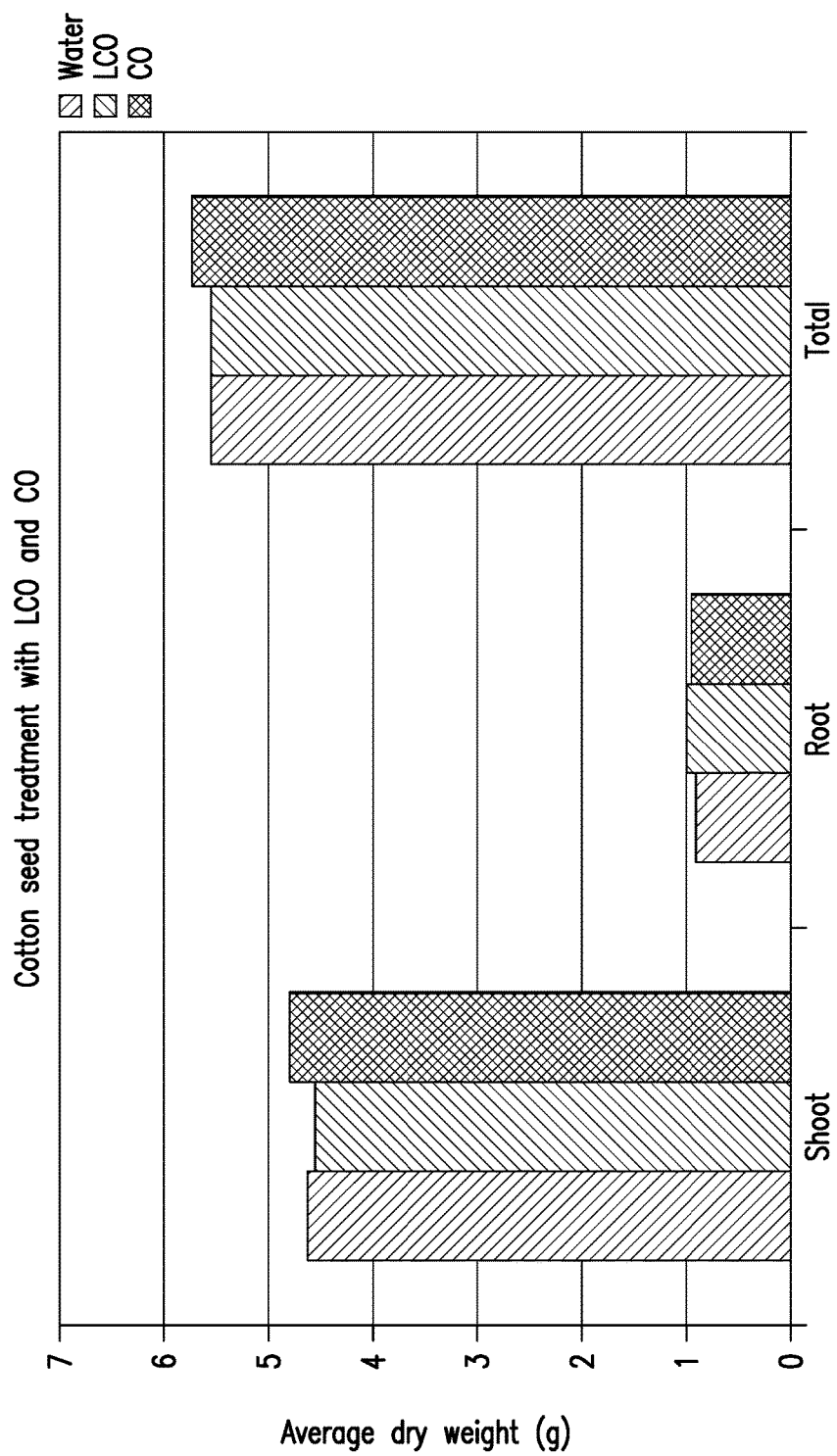
FIG. 26 is a bar graph that illustrates effect of the CO illustrated in FIG. 2a, compared to the LCO illustrated in FIG. 2b, and water, treated on cotton seed, expressed in terms of average plant dry weight.

There were no significant differences in cotton plant dry weight for control, LCO and CO. However, CO produced relatively higher plant dry weight over control and LCO. The total plant dry weight increased by CO over control was 3.29% (FIG. 26).

Example 14: Soybean Foliar Treatment with Various Actives

Soybean plants (Jung seed, var. 8168NRR) were treated with various active molecules at V4 growth stage. Plant were grown from seeds in greenhouse in plastic pots containing 1:1 sand:perlite mixture. Seedlings were grown for 4 wks with occasional liquid fertilizer applications and then the plants were harvested.

Figure 27:
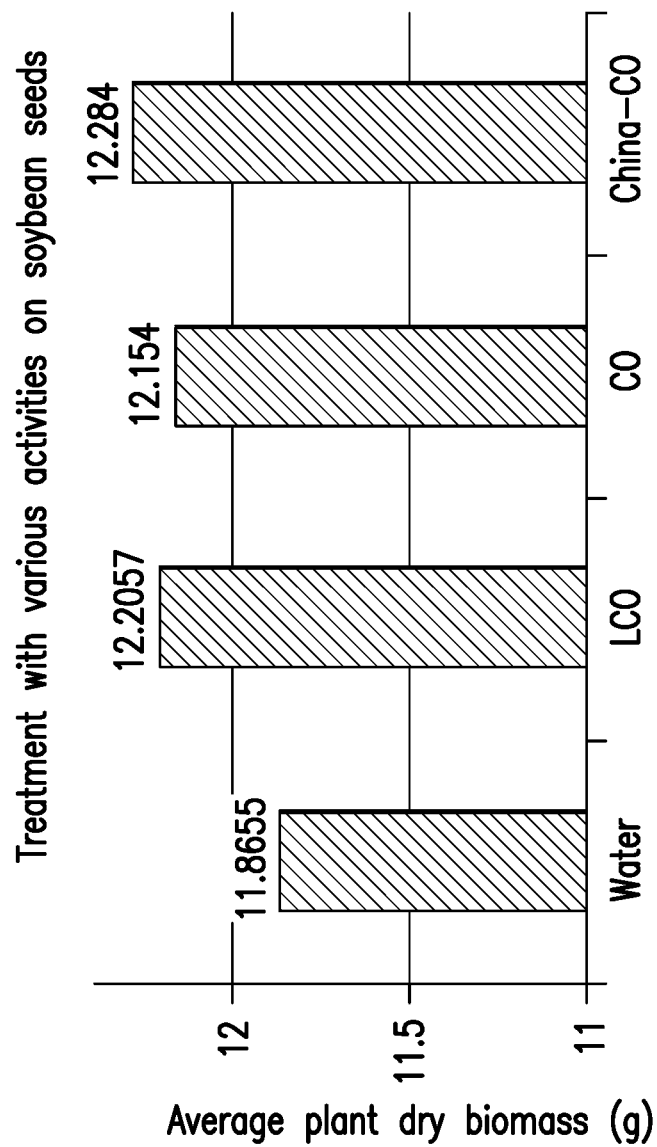
FIG. 27 is a bar graph that illustrates effect of the CO illustrated in FIG. 2a, compared to the LCO illustrated in FIG. 1b, and a mixture of CO's produced by chitinase, treated on soybean plants, expressed in terms of average plant dry biomass.

Foliar application of soybean LCO, Pea CO or China-CO had no significant effect on plant dry biomass increase (FIG. 27). The biomass for each of LCO, CO and China-CO was relatively higher than the control plants, with the actives equally effective.

Example 15: Corn Seed Application

Corn seeds were treated with various combinations of Pea CO ($10^{-8}$ M) and Pea LCO ($10^{-8}$, $10^{-9}$ M). Seeds were planted in greenhouse plastic pots containing 1:1 sand:perlite mixture. Seedlings were harvested 10 days after planting, washed clean and then dried in an oven at 60 C for 48 hr.

Figure 28:
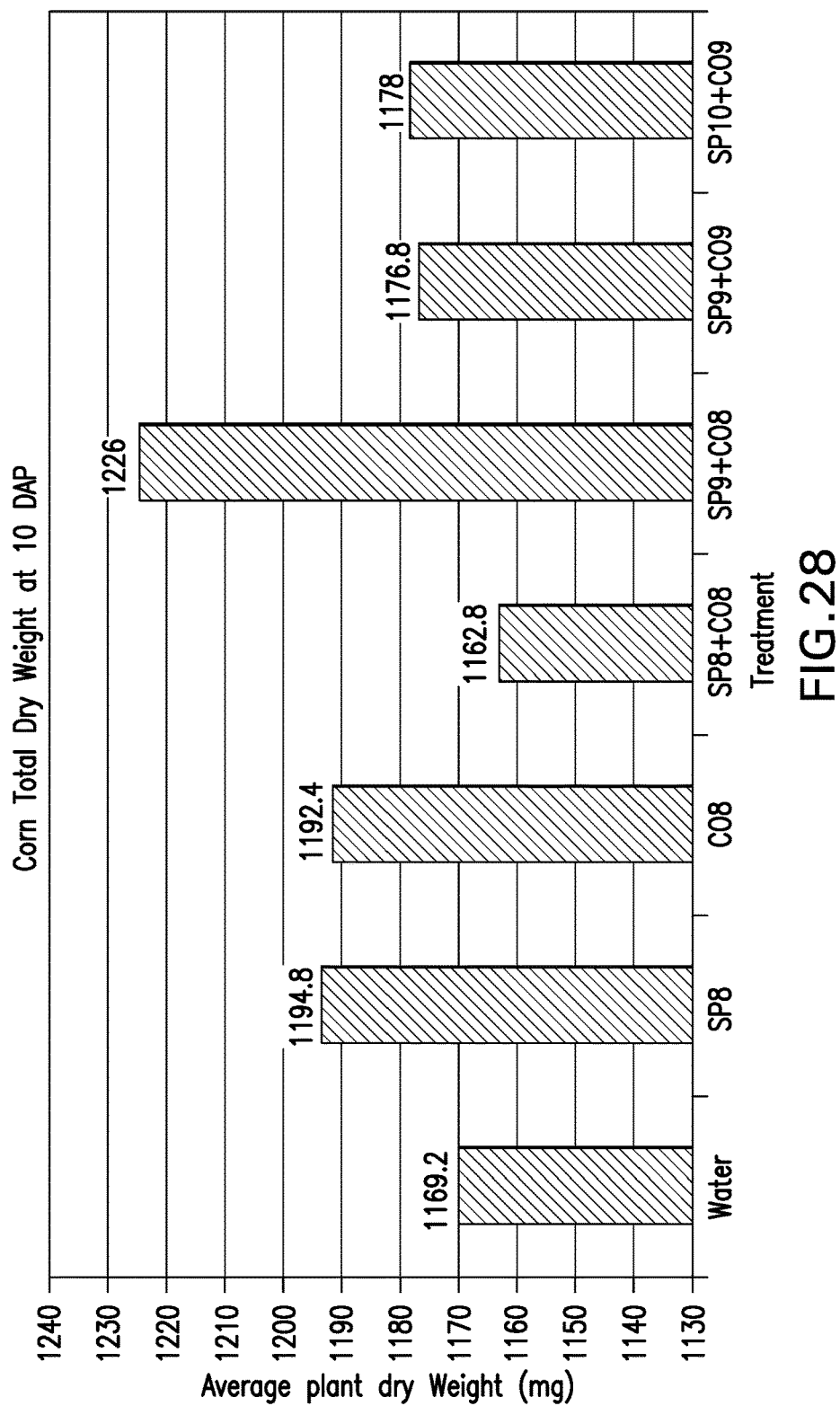
FIG. 28 is a bar graph that illustrates effect of the CO illustrated in FIG. 2a, alone or in combination with the LCO illustrated in FIG. 2b, compared to the LCO illustrated in FIG. 2b and water, treated on corn seed, expressed in terms of average plant dry weight.

As illustrated in FIG. 28, both CO ($10^{-8}$ M) (designated C08) and LCO ($10^{-8}$ M) (designated SP8) alone increased corn seedling dry weight. Only the LCO at $10^{-9}$/C0 at $10^{-8}$ combination increased corn seedling dry weight more than either Pea LCO (SP) or Pea CO.

Example 16: Sorghum Seed Germination in Petriplates

Figure 29:
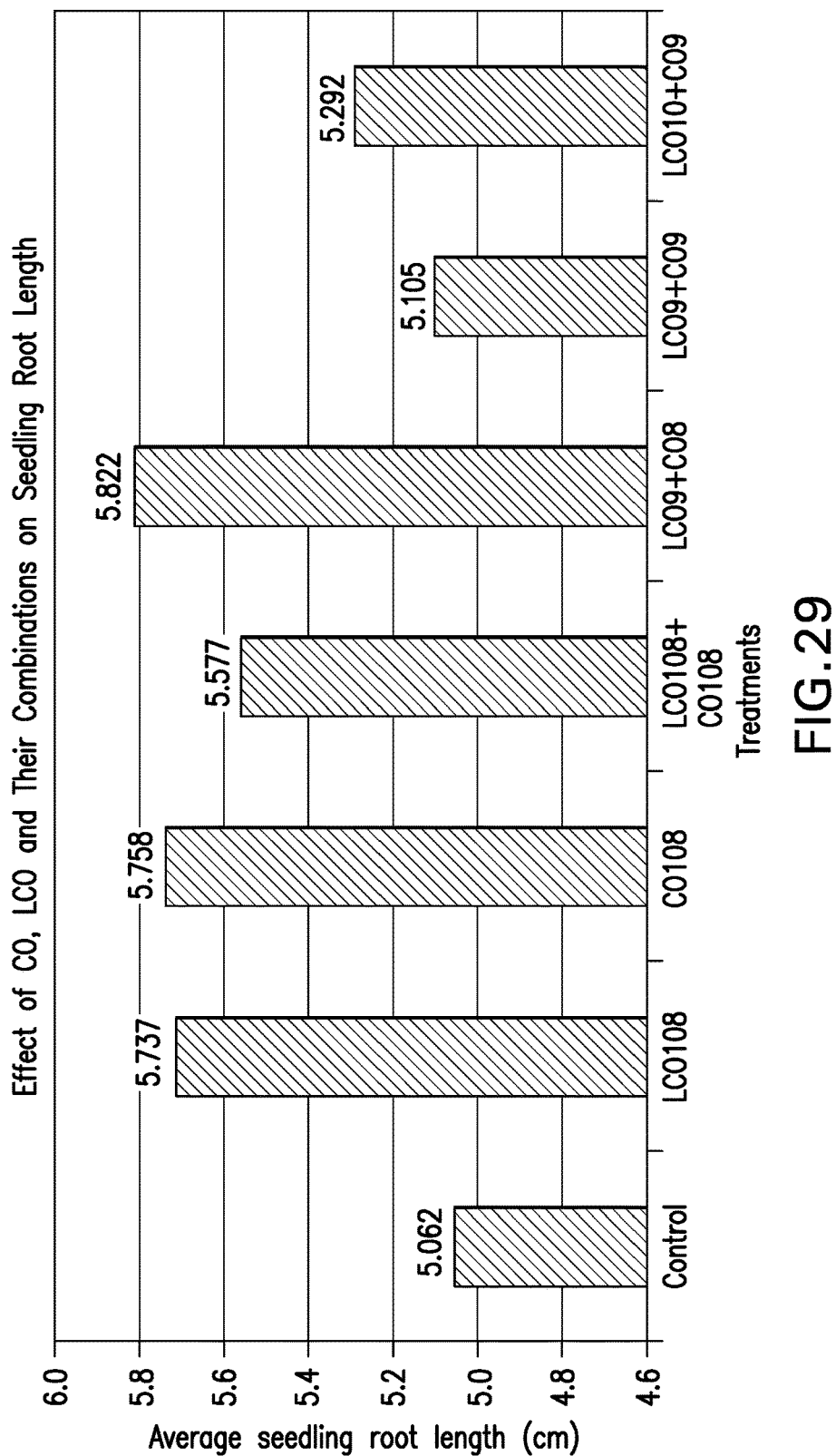
FIG. 29 is a bar graph that illustrates effect of the CO illustrated in FIG. 2a, alone or in combination with the LCO illustrated in FIG. 2b, compared to the LCO illustrated in FIG. 2b and water, treated on sorghum seed, expressed in terms of average seedling root length.

Sorghum seeds were germinated in petriplates containing liquid treatment solutions. Seedlings were harvested after 5 days and their roots were measured using WinRHIZO scanner. As illustrated in FIG. 29, both Pea CO ($10^{-8}$ M) and Pea LCO ($10^{-8}$ M) increased seedling root length and the combination of CO at $10^{-8}$ and LCO at $10^{-9}$ increased seedling root length more than the increase with either CO or LCO alone.

Example 17: Cotton Foliar Application

Cotton plants were grown from seeds in greenhouse plastic pots containing sand:perlite in a 1:1 mixture. When seedlings were at the V-stage, they were foliar-sprayed with Pea CO ($10^{-8}$ M) and CO plus micronutrients (Ca-pantothenate and boric acid), each in minute amounts.

Figure 30:
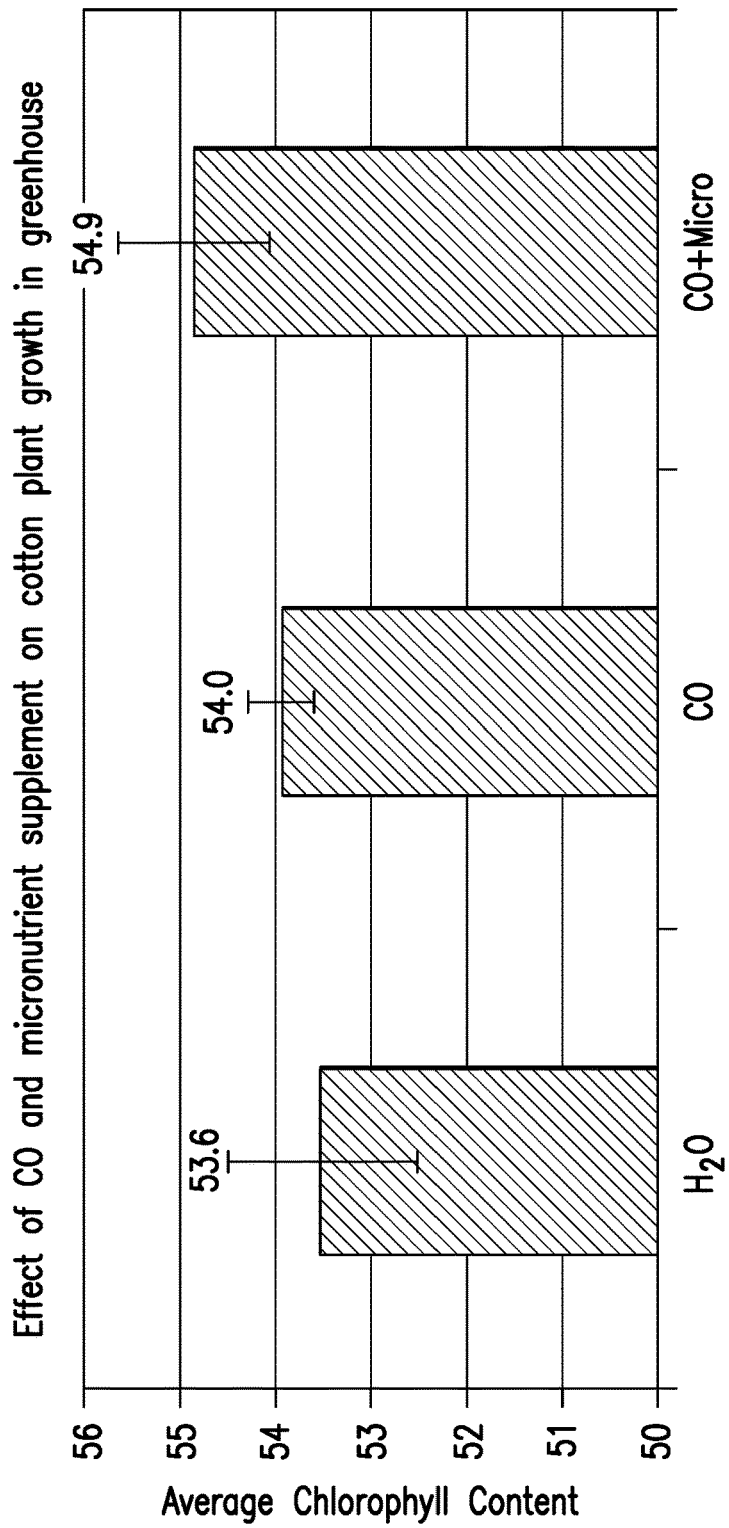
FIG. 30 is a bar graph that illustrates effect of the CO illustrated in FIG. 2a, alone or in combination with a micronutrient, compared to water, treated on cotton plants, expressed in terms of average chlorophyll content.
Figure 31:
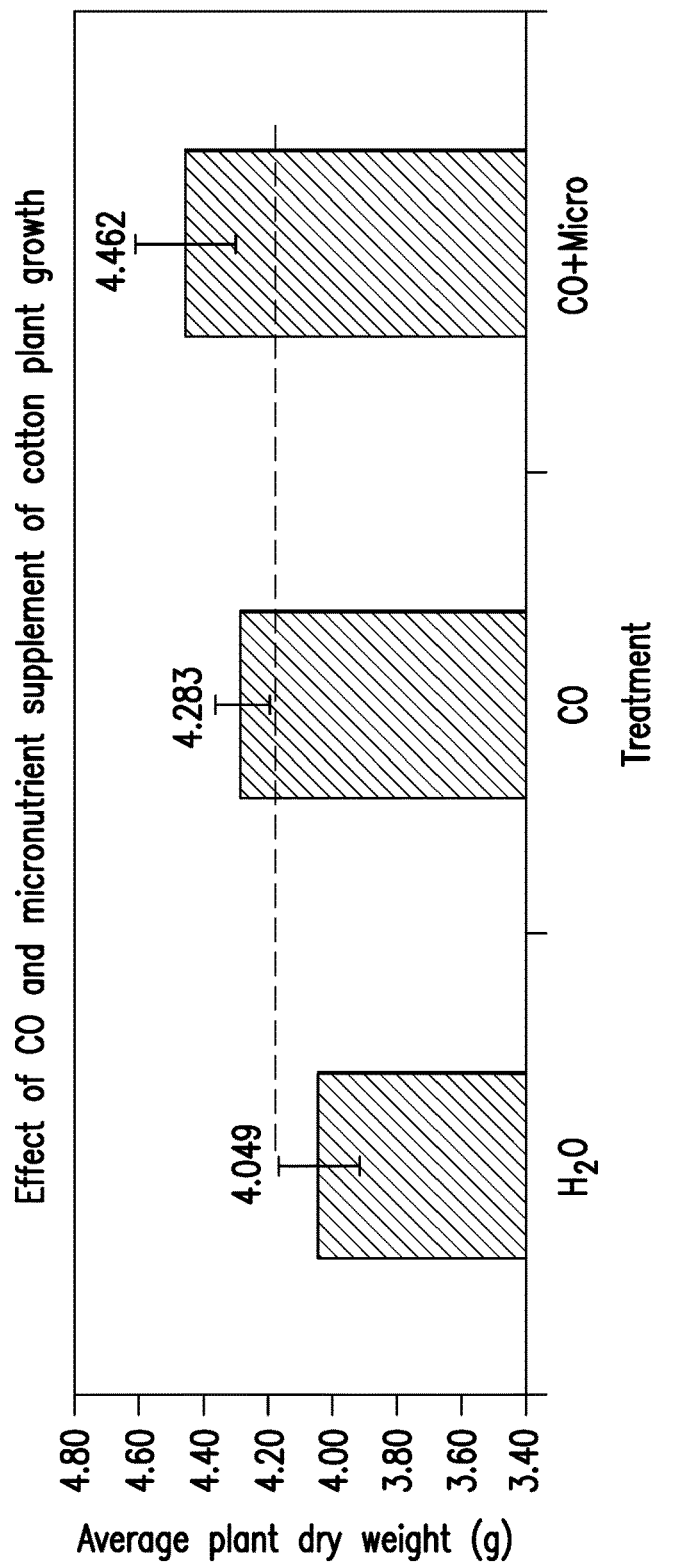
FIG. 31 is a bar graph that illustrates effect of the CO illustrated in FIG. 2a, alone or in combination with a micronutrient, compared to water, treated on cotton plants, expressed in terms of average plant dry weight.

Plants were harvested 4 wks after treatment. Before harvest, leaf greenness was measured by SPAD chlorophyll meter. As illustrated in FIGS. 30 and 31, CO significantly increased leaf greenness and produced a numerical increase in average dry plant weight compared to control, and the combination treatment with CO and micronutrients achieved an even greater increase.

18-20: Field Trials

Example 18: Soybean

Nineteen field trials were conducted to evaluate embodiments of the present invention on grain yield when applied to soybean foliage. The field trials were conducted in eight states with various soil characteristics and environmental conditions.

The treatments used in the trials were control (water), pure CO (chitooligosaccharide)—CO-V (illustrated in FIG. 2a) and pure LCO (lipo-chitooligosaccharide)—SP104 (illustrated in FIG. 2b). CO and LCO treatments were $8\times10^{-8}$ molar concentration resulting in 12 µg/acre applied. Different commercial soybean varieties were employed. Treatments were added to glyphosate herbicide and sprayed on the foliage at plant vegetative stage V4 to V5. Four ounces per acre of the treatment was combined with the herbicide and water was applied at a rate of 5 to 10 gallons per acre. Soybeans were grown to maturity, harvested and grain yield determined.

The results are set forth in Table 1.

|  | | YIELD (bu/A) | |
| --- | --- | --- | --- |
|  | Control | LCO (SP104) | CO (CO-V) |
| Mean (N = 19) | 56.5 | 58.3 | 58.2 |
| Response (bu/A) |  | 1.8 | 1.7 |
| Response Increase (% of Control) |  | 3% | 3% |
| Positive Yield Response (%) |  | 68.4 | 68.4 |

As reflected by comparison between Control and CO, the yield was enhanced by foliar CO treatment by 1.7 bu/A, resulting in a 3% increase over the Control, and a positive yield enhancement occurred in 68.4% of the trials.

In comparison to the foliar LCO response, the CO mean yield was 0.1 bu/A, less, but the same percent yield increase over the Control and the same percent positive yield enhancement. Therefore, both CO and LCO provided substantially equal yield enhancements as a foliar treatment.

Example 19: Corn

Sixteen (16) field trials were conducted to evaluate embodiments of the present invention on grain yield when applied to corn foliage. The field trials were conducted in eight states with various soil characteristics and environmental conditions.

The treatments used in the trials were Control (water), pure CO (chitooligosaccharide)—CO-V (illustrated in FIG. 2a) and pure LCO (lipo-chitooligosaccharide)—SP104 (illustrated in FIG. 2b). Different commercial corn hybrids were employed. Treatments were added to glyphosate herbicide and sprayed on the foliage at the time of normal herbicide application. Four ounces per acre of the treatments were combined with the herbicide, plus water and applied at a rate of 5 to 10 gallons per acre. Corn was grown to maturity, harvested and grain yield determined.

TABLE 2

|  | | YIELD (bu/A) | |
| --- | --- | --- | --- |
|  | Control | LCO (SP104) | CO (CO-V) |
| Mean (N = 16) | 192.6 | 196.8 | 201.8 |
| Response (bu/A) |  | 4.2 | 9.2 |
| Response Increase (% of Control) |  | 2.2 | 4.8 |
| Positive Yield Response (%) |  | 75.0 | 93.8 |

As reflected by comparison between Control and CO, the yield was enhanced by foliar CO treatment by 9.2 bu/A, resulting in a 4.8% yield increase over Control, and a positive yield enhancement occurred in 93.8% of the trials.

In comparison to the foliar LCO response, the CO mean yield was 5.0 bu/A better, providing a 2.6% higher yield increase, and the trials with a positive response was 18.8% better.

Therefore, both CO and LCO provided yield enhancements as a foliar treatment, but the CO performed at least twice better than the LCO.

Example 20: Corn

Ten field trials were conducted to evaluate embodiments of the present invention on grain yield when applied to corn seed before planting. Five field trials were conducted in five states, and five trials were conducted in Argentina.

The treatments used in the trials were Control (water), pure CO (chitooligosaccharide)—CO-V (illustrated in FIG. 2a) and pure LCO (lipo-chitooligosaccharide)—SP104 (illustrated in FIG. 2b). CO and LCO treatments were $1 \times 10^{-8}$ molar concentration resulting in 1 μg/acre applied. Different commercial corn hybrids were employed. Three fluid ounces of the treatment were applied to fifty (50) pounds of seed before planting. Corn was grown to maturity, harvested and grain yield determined.

The results are set forth in Table 3.

|  | YIELD (bu/A) | | |
|---|---|---|---|
|  | Control | LCO (SP104) | CO (CO-V) |
| Mean (N = 10) | 181.5 | 192.6 | 188.0 |
| Response (bu/A) |  | 11.1 | 6.5 |
| Response Increase (% of Control) |  | 6.1 | 3.6 |
| Positive Yield Response (%) |  | 90.0 | 80.0 |

As reflected by comparison between Control and CO, the yield was enhanced by seed application of CO treatment by 6.5 bu/A, resulting in a 3.6% increase over the Control, and a positive yield enhancement occurred in 80.0% of the trials.

In comparison between CO and LCO, the CO mean yield was 4.6 bu/A less, resulting in 2.5% less yield increase above the Control, and 10.0% less positive yield responses amongst the ten trials.

Both the CO and LCO treatments provided yield enhancement above the Control when applied to corn seed, with the LCO providing the highest response.

All patent and non-patent publications cited in this specification are indicative of the level of skill of those skilled in the art to which this invention pertains. All these publications are herein incorporated by reference to the same extent as if each individual publication or patent application were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A composition comprising at least one chitin oligomer in an agriculturally acceptable carrier, said at least one chitin oligomer present in said composition at a concentration of about $10^{-14}$ to about $10^{-5}$ M, wherein said at least one chitin oligomer is not a lipo-chitooligosaccharide.

2. The composition of claim 1, wherein said at least one chitin oligomer comprises a chitin oligomer represented by the formula:

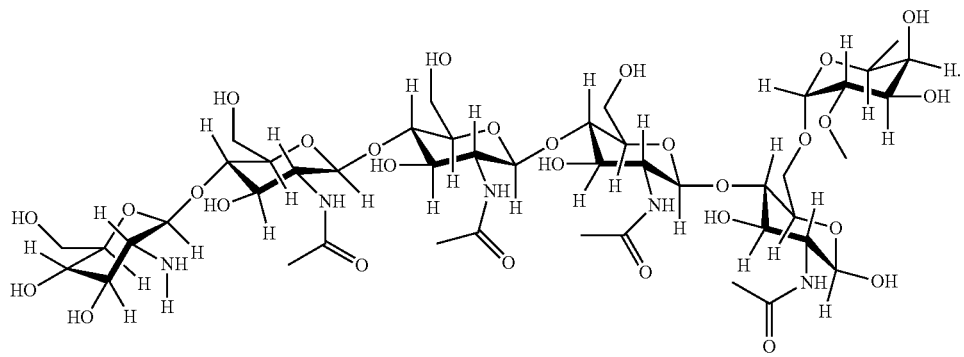

3. The composition of claim 1, wherein said at least one chitin oligomer comprises a chitin oligomer represented by the structure:

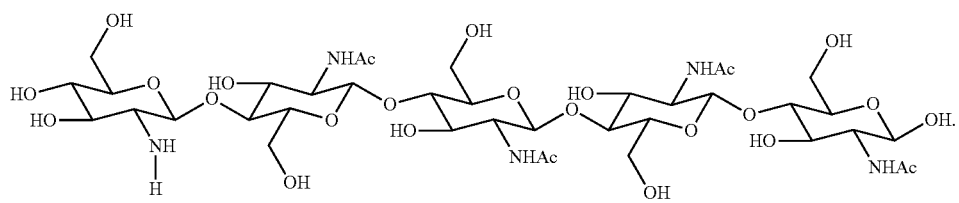 [SMILES: CC(=O)NC1C(O)OC(CO)C(OC2OC(CO)C(OC3OC(CO)C(OC4OC(CO)C(OC5OC(CO)C(O)C(O)C5N)C(O)C4NC(C)=O)C(O)C3NC(C)=O)C(O)C2NC(C)=O)C1O]

4. The composition of claim 1, wherein said at least one chitin oligomer comprises a chitin oligomer represented by the formula:

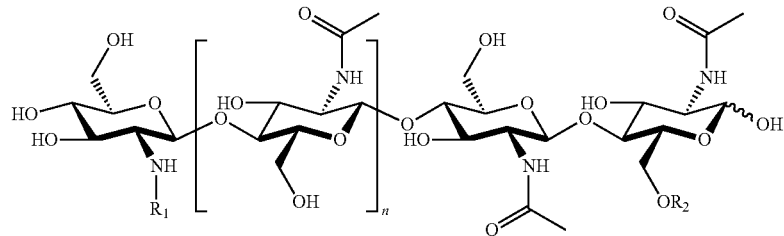

wherein n=1 or 2; $R_1$ represents hydrogen or methyl; and $R_2$ represents hydrogen or $SO_3H$.

5. The composition of claim 1, wherein said at least one chitin oligomer comprises a chitin oligomer represented by the structure:

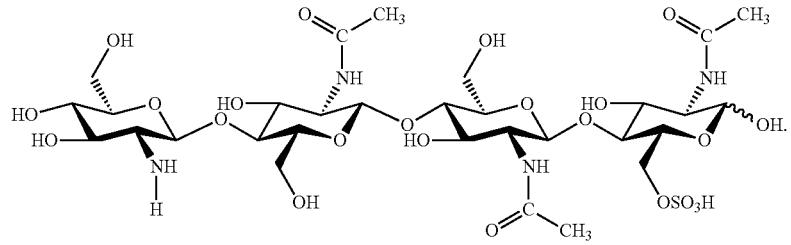

6. The composition of claim 1, wherein said at least one chitin oligomer comprises a chitin oligomer represented by the structure:

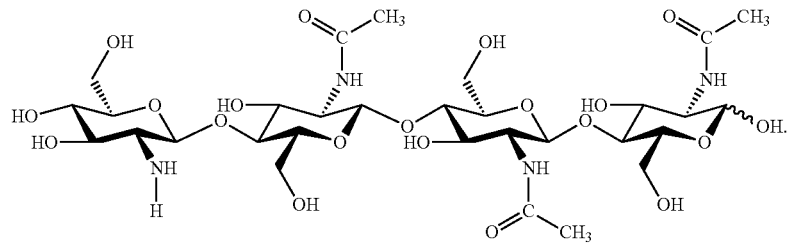

7. The composition of claim 1, wherein said at least one chitin oligomer comprises at least one chitin oligomer represented by the formula:

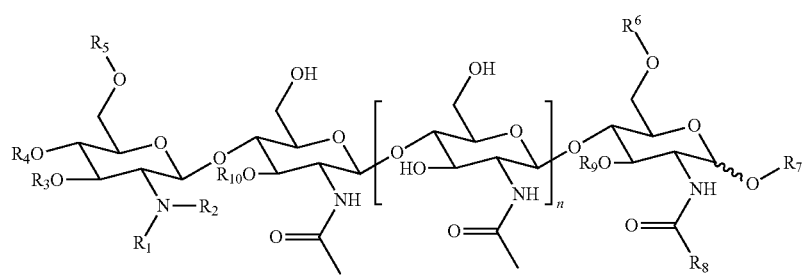

wherein $R_1$ represents hydrogen or methyl; $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-0-S-2-0-MeFuc, 2-0-MeFuc, or 4-0-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3.

8. The composition of claim 1, wherein said at least one chitin oligomer is present in said composition at a concentration of about $10^{-11}$ to about $10^{-5}$ M.

9. The composition of claim 1, wherein said at least one chitin oligomer is present in said composition at a concentration of about $10^{-7}$ to about $10^{-5}$ M.

10. The composition of claim 1, further comprising at least one lipo-chitooligosaccharide (LCO).

11. The composition of claim 1, further comprising at least one chitin.

12. The composition of claim 1, further comprising at least one chitosan.

13. The composition of claim 1, further comprising at least one flavonoid.

14. The composition of claim 1, further comprising at least one fungicide, herbicide and/or insecticide.

15. The composition of claim 1, further comprising at least one phosphate solubilizing microorganism.

16. The composition of claim 1, further comprising at least one diazotroph.

17. A method comprising applying the composition of claim 1 to plant seed in an amount effective to enhance the growth and/or yield of plants grown from said seed.

18. The method of claim 17, wherein the composition of claim 1 is applied to plant seed prior to planting said plant seed in a plant growth medium.

19. A plant seed that has been treated with the composition of claim 1, wherein at least a portion of said at least one chitin oligomer remains on the surface of said plant seed.

20. A method comprising applying the composition of claim 1 to soil at a rate of about 1 to about 30 μg per acre.

* * * * *